(12) United States Patent
Kawayoke

(10) Patent No.: US 12,426,882 B2
(45) Date of Patent: Sep. 30, 2025

(54) CLIP UNIT, CLIP DELIVERY DEVICE, AND LOADING METHOD OF CLIP UNIT

(71) Applicant: OLYMPUS MEDICAL SYSTEMS CORP., Tokyo (JP)

(72) Inventor: Shoichiro Kawayoke, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 409 days.

(21) Appl. No.: 18/115,173

(22) Filed: Feb. 28, 2023

(65) Prior Publication Data

US 2023/0277177 A1 Sep. 7, 2023

Related U.S. Application Data

(60) Provisional application No. 63/315,496, filed on Mar. 1, 2022.

(51) Int. Cl.
*A61B 17/08* (2006.01)
*A61B 17/10* (2006.01)

(52) U.S. Cl.
CPC ............ *A61B 17/083* (2013.01); *A61B 17/10* (2013.01)

(58) Field of Classification Search
CPC ....... A61B 17/083; A61B 17/10; A61B 17/12; A61B 17/122; A61B 17/128; A61B 17/1285; A61B 2017/00955; A61B 2017/0034; A61B 2090/037
See application file for complete search history.

(56) References Cited

U.S. PATENT DOCUMENTS

| 11,259,815 | B2 * | 3/2022 | Han | A61B 17/1222 |
|---|---|---|---|---|
| 2020/0060685 | A1 | 2/2020 | Han et al. | |
| 2023/0225742 | A1 * | 7/2023 | Yuasa | A61B 18/1445 606/142 |
| 2023/0277177 | A1 * | 9/2023 | Kawayoke | A61B 17/083 606/142 |
| 2024/0041449 | A1 * | 2/2024 | Kawayoke | A61B 17/083 |

* cited by examiner

*Primary Examiner* — Ryan J. Severson
(74) *Attorney, Agent, or Firm* — Morgan, Lewis & Bockius LLP

(57) ABSTRACT

A clip unit comprises a clip and a tube. the clip includes a plurality of arms movable between an open position and a closed position. The tube includes a tube main body configured to contain at least a part of the clip, a first wing, and a second wing. The first wing is connected to the tube main body and the second wing is connected to the first wing. The first wing is elastically deformable relative to the tube main body in a radial direction of the tube main body, and the first wing is biased radially inward toward an inner region of the tube main body. The second wing is elastically deformable relative to the first wing in the radial direction of the tube main body, and the second wing is biased radially outward toward an outside of the tube main body.

20 Claims, 19 Drawing Sheets

CLIP UNIT, CLIP DELIVERY DEVICE, AND LOADING METHOD OF CLIP UNIT

CROSS-REFERENCE TO RELATED APPLICATIONS

The present disclosure claims priority on U.S. Provisional Application No. 63/315,496, filed Mar. 1, 2022. The disclosure of the prior applications is hereby incorporated by reference herein in its entirety.

TECHNICAL FIELD

The present disclosure relates to a clip unit, a clip delivery device, and a loading method of a clip unit.

BACKGROUND

In an endoscopic treatment, a clip unit capable of ligating the dissection portion or the like after the treatment to realize the hemostasis or the like is used. The clip unit includes a clip configured to clamp the dissection portion or the like and a pressing tube configured to accommodate the clip and lock the clip in a closed state. The clip unit is introduced to the treatment portion by an applicator that is insertable into a channel of the endoscope.

The clip system disclosed in United States Patent Application, Publication No. 2020/0060685 A1 includes a clip unit (end effector) and an applicator (delivery device) having the mechanism into which the clip unit is loadable and from which the clip unit is detachable. A pressing pipe of the clip unit includes a wing at the proximal-end side, and clip unit and the applicator are connected with each other by coupling the wing of the pressing pipe with the applicator. The clip system is configured to be capable of reloading (reloadable) a new clip unit to the applicator after indwelling the clip unit in the living body.

SUMMARY

A clip unit comprises a clip and a tube. the clip includes a plurality of arms movable between an open position and a closed position. The tube includes a tube main body configured to contain at least a part of the clip, a first wing, and a second wing. The first wing is connected to the tube main body and the second wing is connected to the first wing. The first wing is elastically deformable relative to the tube main body in a radial direction of the tube main body, and the first wing is biased radially inward toward an inner region of the tube main body. The second wing is elastically deformable relative to the first wing in the radial direction of the tube main body, and the second wing is biased radially outward toward an outside of the tube main body.

A clip delivery device comprises a sheath and a clip. The clip includes a plurality of arms movable between an open position and a closed position. The clip delivery device further comprises a tube. The tube includes a tube main body configured to contain at least part of the clip, a first wing, and a second wing. The clip delivery device further comprises a connector inserted into the tube main body and detachably connected to the clip, and a wire inserted into the sheath and detachably connected the connector. The first wing is connected to the tube main body and the second wing is connected to the first wing. The first wing is elastically deformable relative to the tube main body in a radial direction of the tube main body, and the first wing is biased radially inward toward an inner region of the tube main body. The second wing is elastically deformable relative to the first wing in the radial direction of the tube main body, and the second wing is biased radially outward toward an outside of the tube main body.

A method of loading a clip unit into an applicator comprises connecting the clip unit and a wire, wherein the clip unit includes a clip, a tube configured to contain at least part of clip, and wherein the tube includes a first elastic portion, pulling the wire proximal to a sheath, wherein the wire is inserted through the sheath through, and housing the tube in the sheath. When housing the tube in the sheath, a distal end of the first elastic portion presses in a radially inward direction of the tube.

DETAILED DESCRIPTION

First Embodiment

A clip delivery device according to a first embodiment of the present disclosure will be described with reference from FIG. 1 to FIG. 12.

[Clip Delivery Device 300]

The clip delivery device (clip system, clip device) 300 includes a clip introduction device (applicator) 200 and a clip unit 1. The clip unit 1 is loaded into the clip introduction device 200.

[Clip Introduction Device 200]

Figure 1:
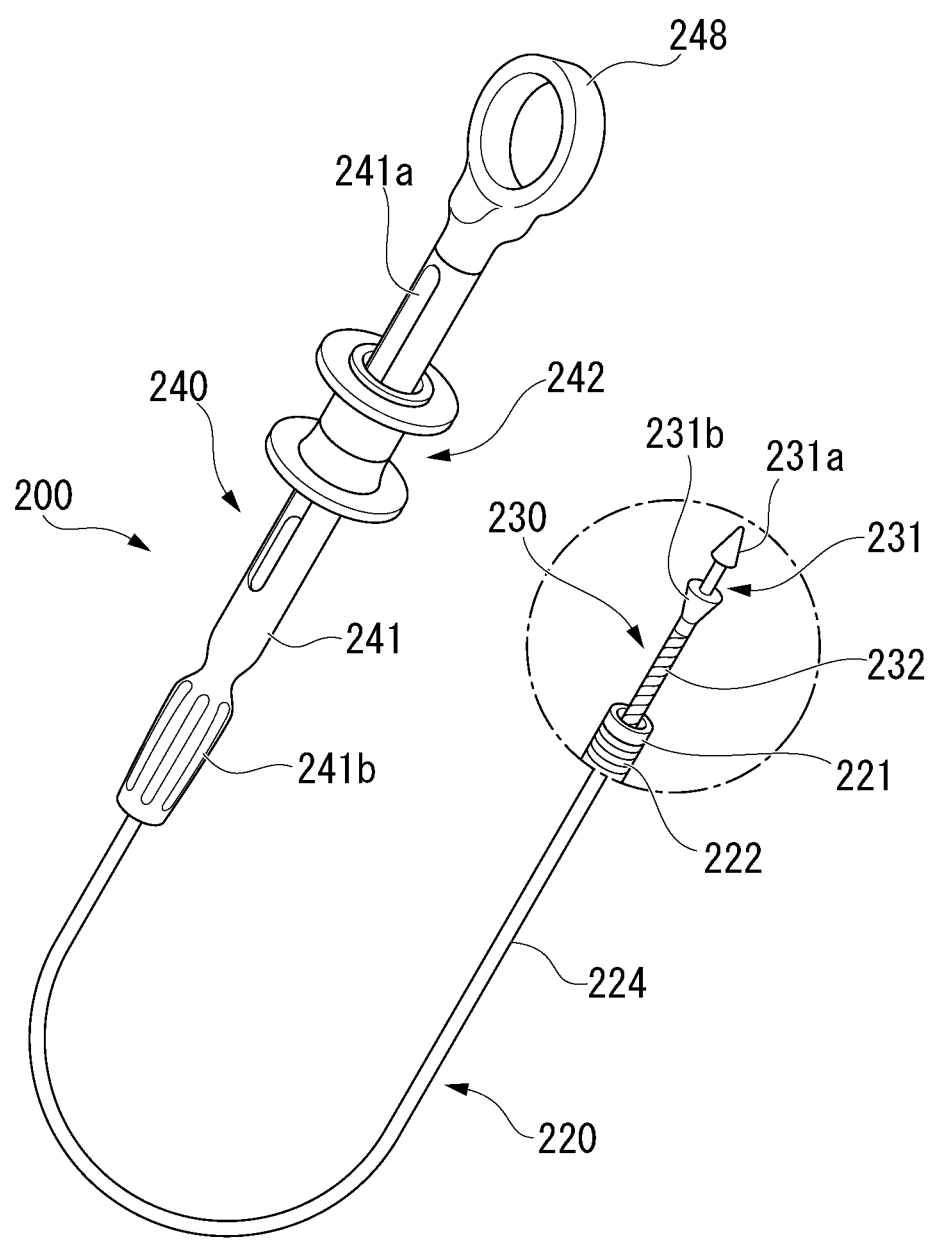
FIG. 1 is a view showing a clip introduction device of a clip delivery device according to a first embodiment.

FIG. 1 is a view showing the clip introduction device 200.

The clip introduction device (applicator) 200 includes a sheath 220, an operation wire 230, and an operation portion 240.

In the following description, the clip unit 1 side in the longitudinal direction A of the clip delivery device 300 is referred to as a tip-end side (distal-end side) A1 of the clip delivery device 300, and the operation portion 240 side of the clip introduction device 200 is referred to as a base-end side (proximal-end side) A2 of the clip delivery device 300.

The clip introduction device 200 is, for example, inserted through the treatment device insertion channel of the endoscope to be used in combination with the endoscope. Accordingly, the sheath 220 is formed to be enough longer than the length of the treatment device insertion channel of the endoscope. The sheath 220 has the flexibility and is configured to bend following the bending of the insertion portion of the endoscope.

The sheath 220 includes a distal-end tip 221, a distal-end coil 222, and a hand-side coil 224, and the entire of the sheath 220 is formed in an elongated tubular shape. The distal-end coil 222 is disposed at the distal-end portion side of the sheath 220. The distal-end tip 221 is disposed in the distal-end portion of the distal-end coil 222.

The operation wire (power transmission member) 230 includes an engagement portion 231a in an approximately conical shape and engaging with the clip unit 1, and a wire connection portion 231b provided at the proximal end of the engagement portion 231a. An arrowhead hook 231 is formed of metal material such as the stainless steel or the like, for example.

The arrowhead 231 is provided at the distal end of the operation wire (power transmission member) 230, and formed in the approximately conical shape. The arrowhead hook 231 is formed of metal material such as the stainless steel or the like, for example.

The wire 232 is inserted to be freely advanceable and retractable with respect to the sheath 220. The distal-end portion of the wire 232 is fixed to the proximal end of the wire connection portion 231b by welding or the like, for example.

As shown in FIG. 1, the operation portion 240 includes an operation portion main body 241, a slider 242, and a thumb ring 248. The operation portion main body 241 is injection-molded, for example, from a resin material. The operation portion main body 241 includes a slit portion 241a, and a rotation grip 241b at the distal-end side. The slit portion 241a supports the slider 242 to be advanceable and retractable.

The slider 242 is attached to the operation portion main body 241 to be advanceable and retractable in the longitudinal direction, and to which the proximal end of the wire 232 is attached. By the slider 242 advancing and retracting along the operation portion main body 241, the wire 232 advances and retracts with respect to the sheath 220 and the arrowhead hook 231 advances and retracts.

The thumb ring 248 is attached to the proximal end of the operation portion main body 241 to be rotatable around the longitudinal direction of the operation portion main body 241.

[Clip Unit 1]

Figure 2:
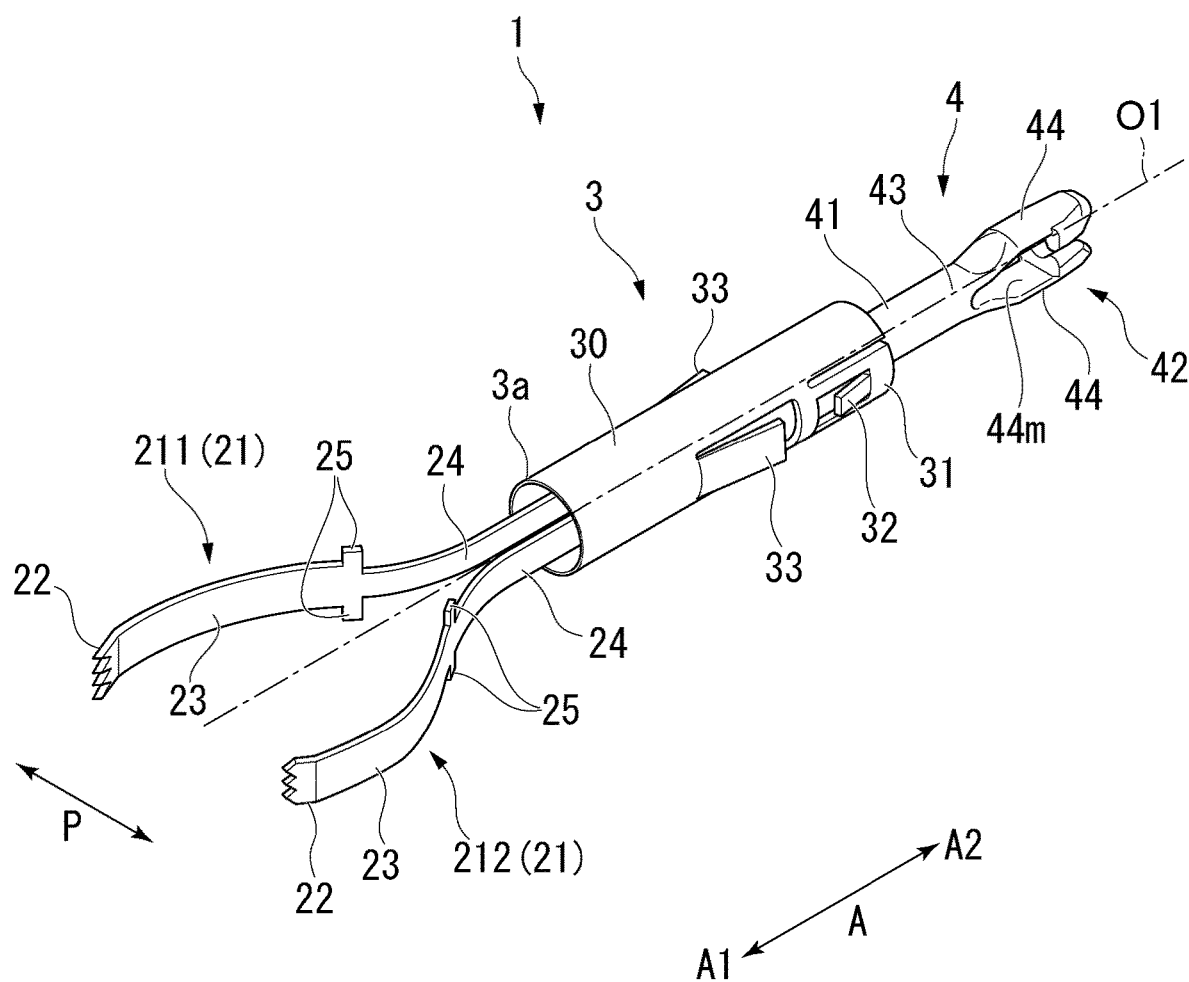
FIG. 2 is a perspective view showing the clip unit.
Figure 3:
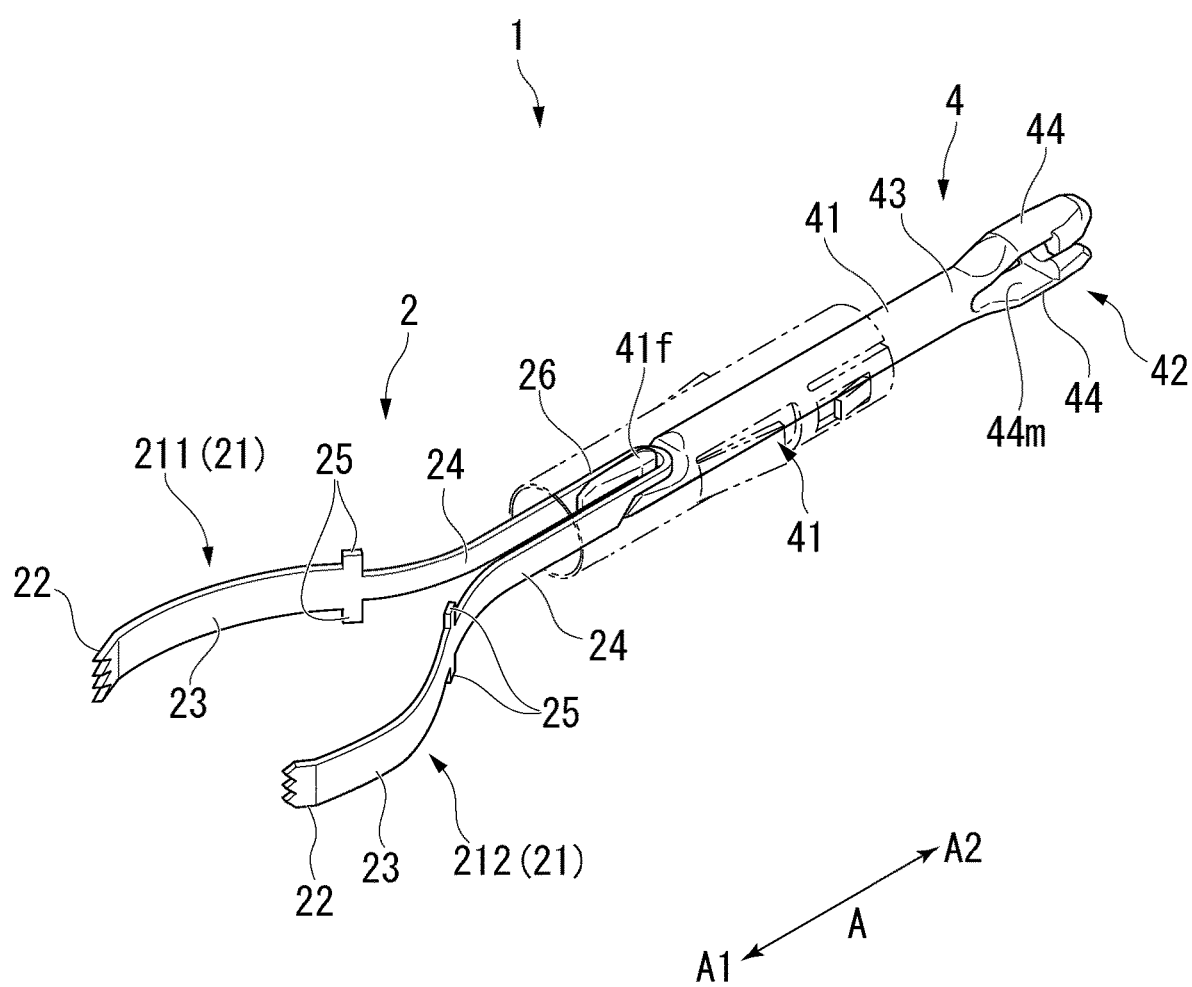
FIG. 3 is a perspective view showing a clip connected to a connection member.

FIG. 2 is a perspective view showing the clip unit 1. FIG. 3 is a perspective view connected to the connection member 4. The clip unit 1 includes the clip 2, the pressing tube 3, and the connection member 4. The proximal-end side A2 of the clip 2 is inserted into the internal space of the pressing tube 3.

The clip 2 includes a pair of arms 21 that can be opened and closed toward the distal-end side A1, and a proximal-end portion 26 provided on the proximal-end side A2 of the pair of arms 21. The clip 2 is detachably connected to an arrowhead hook 231 of the operation wire 230 being inserted through the sheath 220.

The pair of arms 21 has a first arm 211 and a second arm 212. The first arm 211 and the second arm 212 are arranged symmetrically with respect to a central axis O1 in the longitudinal direction A of the clip unit 1. It is noted that the clip 2 may have three or more arms.

The first arm 211 and the second arm 212 have a claw 22, a grasping portion 23, a sliding portion 24, and an engaging portion 25 arranged from the distal-end side A1 toward the proximal-end side A2.

The claw 22 is formed by bending the distal ends of the first arm 211 and the second arm 212 inwardly. The grasping portion 23 is formed in a substantially flat plate shape and is a portion that grasps the tissue. The sliding portion 24 is a portion that is elastically deformed when the pair of arms 21 is retracted into the pressing tube 3.

The engaging portion 25 is a portion that is engageable with the inner circumferential surface 37 of the pressing tube 3. The engaging portion 25 is a convex portion that protrudes from the grasping portion 23. Specifically, the engaging portion 25 protrudes to both sides in the up-down direction perpendicular to the longitudinal direction A and the open-close direction P of the pair of arms 21.

The proximal-end portion 26 is bent to be formed in a U shape, and is connected to the connection member 4. The proximal-end portion 26 may be bent to be formed in a semi oval. The proximal-end portion 26 and the sliding portion 24 are biased such that the pair of arms 21 are in an open state. Therefore, the pair of arms 21 of the clip 2 have a self-expanding force in the open-close direction P.

Figure 4:
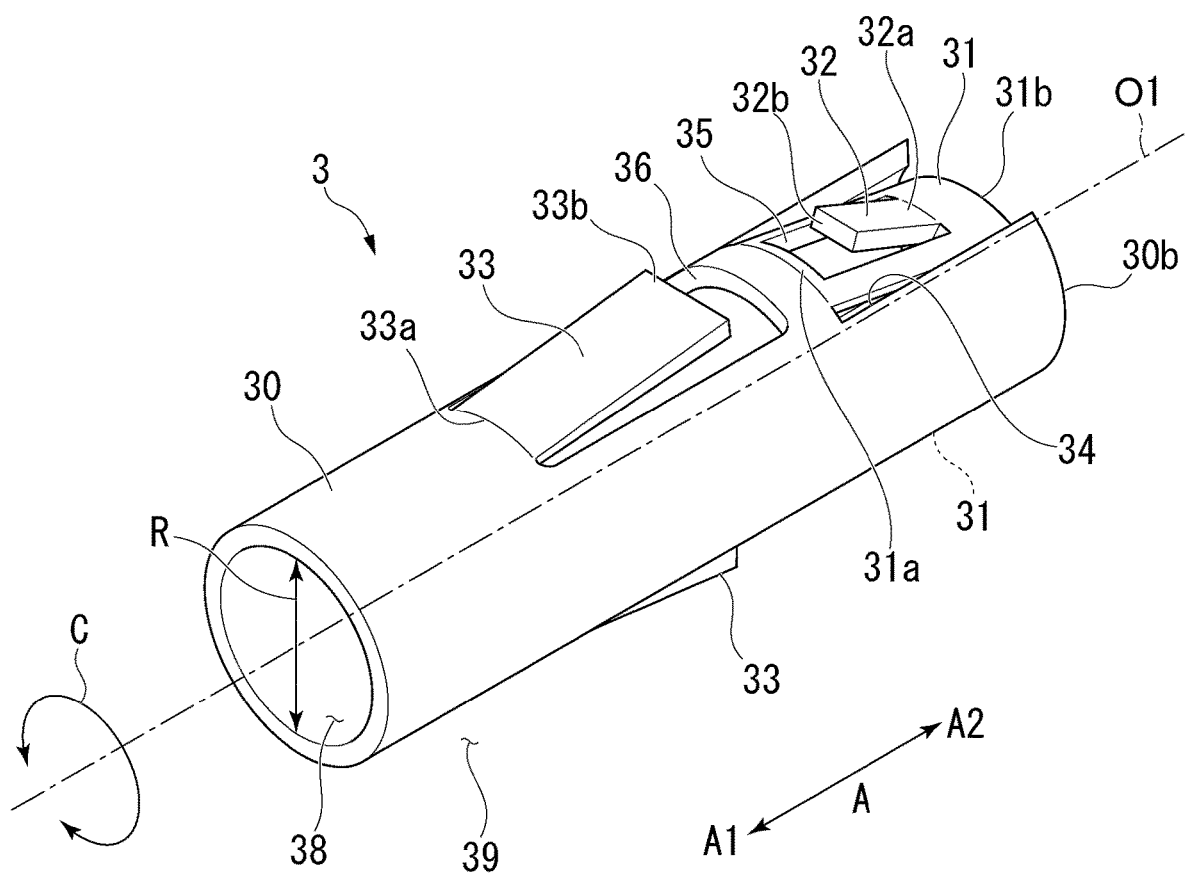
FIG. 4 is a perspective view showing a pressing tube of the clip unit.

FIG. 4 is a perspective view of the pressing tube 3.

The pressing tube (tubular member, tube) 3 is a circular tubular member capable of accommodating at least part of the clip 2. The pressing tube 3 can fix the clip 2 in the closed state that is retracted into the internal space thereof. The pressing tube 3 includes a pressing tube main body 30 formed in a cylindrical shape, a first wing 31, a second wing 32, and a third wing 33.

A pressing tube main body (tubular member main body, tube main body) 30 is formed in a cylindrical shape, and the connection member 4 is advanceable and retractable there-through. An inner region 38 is defined as an inner region in the radial direction R of the pressing tube main body 30, and an outer region 39 is defined as an outer region in the radial direction R. Specifically, the inner region 38 is a region whose distance from the central axis O1 is equal to or less than the outer radius of the pressing tube main body 30. The outer region 39 is a region whose distance from the central axis O1 is larger than the outer radius of the pressing tube main body 30. It is noted that the pressing tube main body 30 may be formed in a tubular shape, for example, may be formed in a square tubular shape.

A first opening 34 and a third opening 36 penetrating in the radial direction R and are formed in the pressing tube main body 30. The first opening 34 is an opening continuous with the proximal end 30b of the pressing tube main body 30, and is provided on both sides of the central axis O1 to sandwich the central axis O1. The third opening 36 is formed on the distal-end side A1 from the first opening 34 and provided on both sides of the central axis O1 to sandwich the central axis O1. The first opening 34 and the third opening 36 are formed at the same position in the circumferential direction C of the pressing tube main body 30.

The pressing tube main body 30 is formed by performing the injection molding using a material more flexible than that of the clip 2, for example, the thermoplastic resin such as PPA (polyphthalamide), PA (polyamide), PEEK (polyetheretherketone), LCP (liquid crystal polymer), and the like having appropriate elasticity. It is noted that the pressing tube main body 30 may be made of the metal instead of the thermoplastic resin.

The first wing 31 is supported by the pressing tube main body 30 so as to be elastically deformable in the radial direction R, and is biased to be arranged in the inner region 38 of the pressing tube main body 30 in a state in which no external force is applied thereto. Two first wings 31 are provided in the pressing tube main body 30 to be on both sides of the central axis O1 to sandwich the central axis O1 therebetween. The first wing 31 is formed in a rectangular shape when viewed from the radial direction R.

The first wing 31 is supported by the pressing tube main body 30 on the distal-end side A1. Specifically, a first fixed end 31a on the distal-end side A1 of the first wing 31 is supported by the pressing tube main body 30. A first free end 31b on the proximal-end side A2 of the first wing 31 is elastically deformable in the radial direction R. The first wing 31 is arranged at a position overlapping the first opening 34 when viewed in the radial direction R, and does not come into contact with the pressing tube main body 30 even in the case of being elastically deformed in the radial direction R.

A second opening 35 penetrating in the radial direction R is formed in the first wing 31 in the vicinity of the center of the first wing 31.

The second wing 32 is supported by the first wing 31 to be elastically deformable in the radial direction R, and biased to be arranged on the outside in the radial direction R of the first wing 31 in the state where no external force is applied thereto. The two first wings 31 support the second wings 32 respectively and the two second wings 32 are provided on both sides of the central axis O1 to sandwich the central axis O1. The second wing 32 is formed in a rectangle shape when viewed in the radial direction R.

The second wing 32 is supported by the first wing 31 on the proximal-end side A2. Specifically, the second fixed end 32a on the proximal-end side A2 of the second wing 32 is supported by the first wing 31. The second free end (end portion at the distal-end side) 32b on the distal-end side A1 of the second wing 32 is elastically deformable in the radial direction R. The second wing 32 is disposed at a position overlapping the second opening 35 when viewed in the radial direction R, and does not contact the first wing 31 even in the case of being elastically deformed in the radial direction R.

When the first wing 31 is disposed in the inner region 38 in the state of receiving no external force, the second free end 32b of the second wing 32 is disposed in the inner region 38. The entire second wing 32 is disposed in the inner region 38. It is noted that the inner region 38 is the region where the distance from the central axis O1 is equal to or less than the outer radius of the pressing tube main body 30 such that the inner region 38 includes the region of the first opening 34 penetrating the pressing tube main body 30.

The third wing 33 is supported by the pressing tube main body 30 so as to be elastically deformable in the radial direction R, and is biased to be arranged in the outer region 39 of the pressing tube main body 30 in a state in which no external force is applied thereto. Two third wings 33 are provided in the pressing tube main body 30 to be on both sides of the central axis O1 to sandwich the central axis O1 therebetween. The third wing 39 is formed in a rectangular shape when viewed from the radial direction R.

The third wing 33 is supported by the pressing tube main body 30 on the distal-end side A1. Specifically, a third fixed end 33a on the distal-end side A1 of the third wing 33 is supported by the pressing tube main body 30. A third free end 33b on the proximal-end side A2 of the third wing 33 is elastically deformable in the radial direction R. The third wing 31 is arranged at a position overlapping the third opening 36 when viewed in the radial direction R, and does not come into contact with the pressing tube main body 30 even in the case of being elastically deformed in the radial direction R.

The third wing 33 is disposed at the distal-end side A1 of the second wing 32. In the present embodiment, the first wing 31 and the third wing 33 are formed at the same position in the circumferential direction C of the pressing tube main body 30.

As shown in FIG. 3, the connection member 4 is connected to the proximal-end portion 26 of the clip 2 so as to be separatable therefrom. Also, the connection member 4 is connected to the arrowhead hook 231 inserting through the sheath 220 so as to separatable therefrom. In other words, the connection member 4 connects the clip 2 and the arrowhead hook 231. The connection member 4 includes an insertion portion 41 being inserted into the inner region 38 of the pressing tube main body 30, and a connection portion 42 provided at the proximal end of the insertion portion 41.

The insertion portion 41 includes a hook 41f in the distal-end portion thereof. The hook 41f is a hook extending in a direction perpendicular to the central axis O1, and is formed in a substantially columnar rod shape. The proximal-end portion 26 of the clip 2 is hooked on the hook 41f. The hook 41f is broken when the proximal-end portion 26 is pulled to the proximal-end side and a tensile breaking force amount of, for example, 20N (Newton) to 60N is applied to the hook 41f.

The connection portion 42 is an engagement portion to which the arrowhead hook 231 of the clip introduction device 200 is engaged (connected). The connection portion 42 includes a connection portion main body 43 and an elastic arm portion 44.

The elastic arm portion 44 is provided at the proximal end of the connection portion main body 43 and is divided into a bifurcated shape. The elastic arm portion 44 is elastically deformable with respect to the connection portion main body 43 and is openable and closable with respect to the connection portion main body 43. A notch portion 44m for gasping and accommodating the engagement portion 231a of the arrowhead hook 231 is formed in the elastic arm portion 44. The notch portion 44m is formed in a shape that closely contacts the outer circumferential surface of the engagement portion 231a of the arrowhead hook 231.

[Operations and Effect of Clip Delivery Device 300]

Next, the operations and effect of the clip delivery device 300 will be described by referring from FIG. 5 to FIG. 10.

Figure 5:
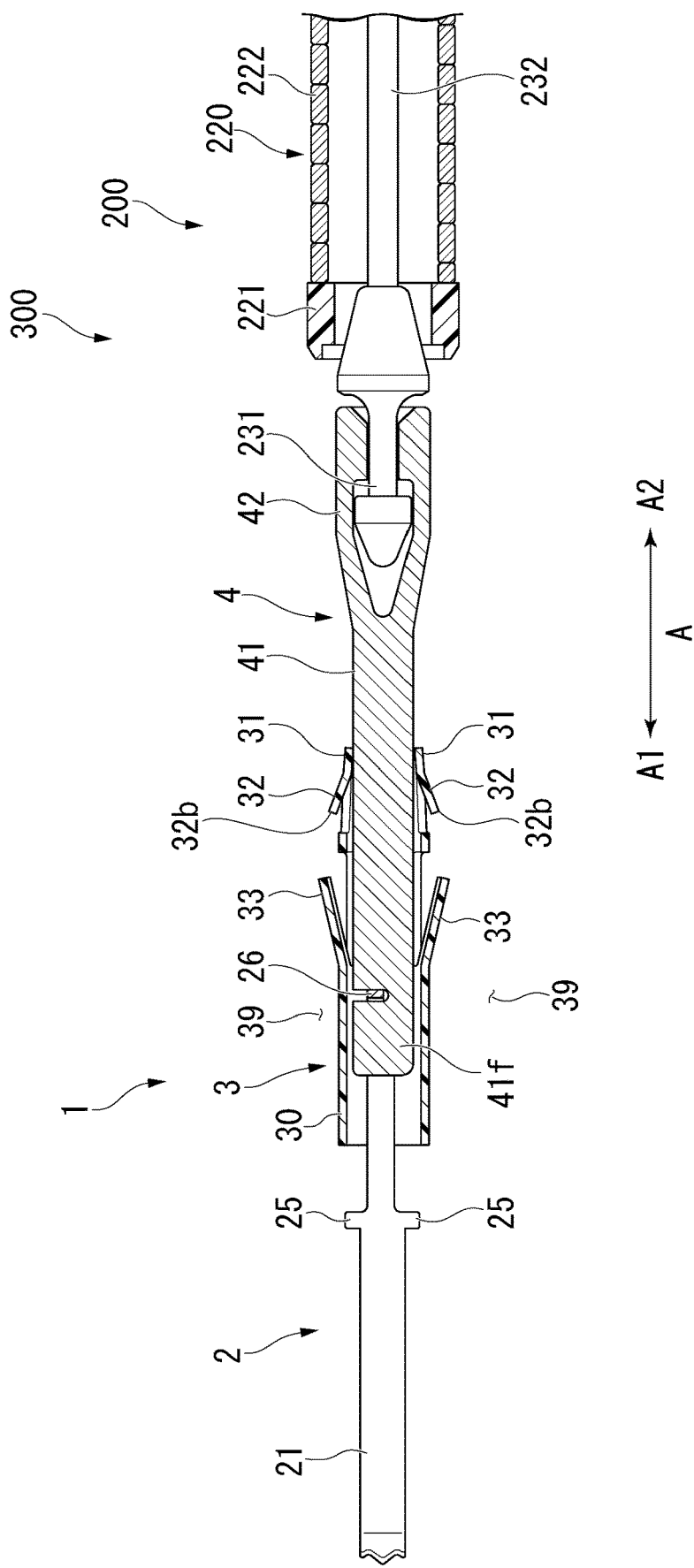
FIG. 5 is a cross-sectional view showing the clip unit that is loaded into the clip introduction device.

FIG. 5 is a cross-sectional view showing the clip unit 1 that is loaded into the clip introduction device 200.

The manufacturer of the clip unit 1 inserts the connection member 4 into the pressing tube 3 from the proximal-end side A2 to connect the clip 2 and the connection member 4 (connection step).

The first wing 31 is coupled with the connection member 4 inserting through the pressing tube main body 30 and pressed outside in the radial direction R. The second wing 32 is in the state of receiving no external force; however, the first wing 31 is pressed outside in the radial direction R such that at least the second free end 32b is pressed outside to the outer region 39. The third wing 33 is in the state of receiving no external force and is arranged in the outer region 39.

The user prepares the new clip unit 1 to be used. The user advances the operation wire 230 to protrude the arrowhead hook 231 toward the distal-end side A1 from the distal-end tip 221 so as to connect the connection portion 42 of the connection member 4 of the clip unit 1 with the arrowhead hook 231. As a result, the clip unit 1 is loaded into the clip introduction device 200 (load step).

Figure 6:
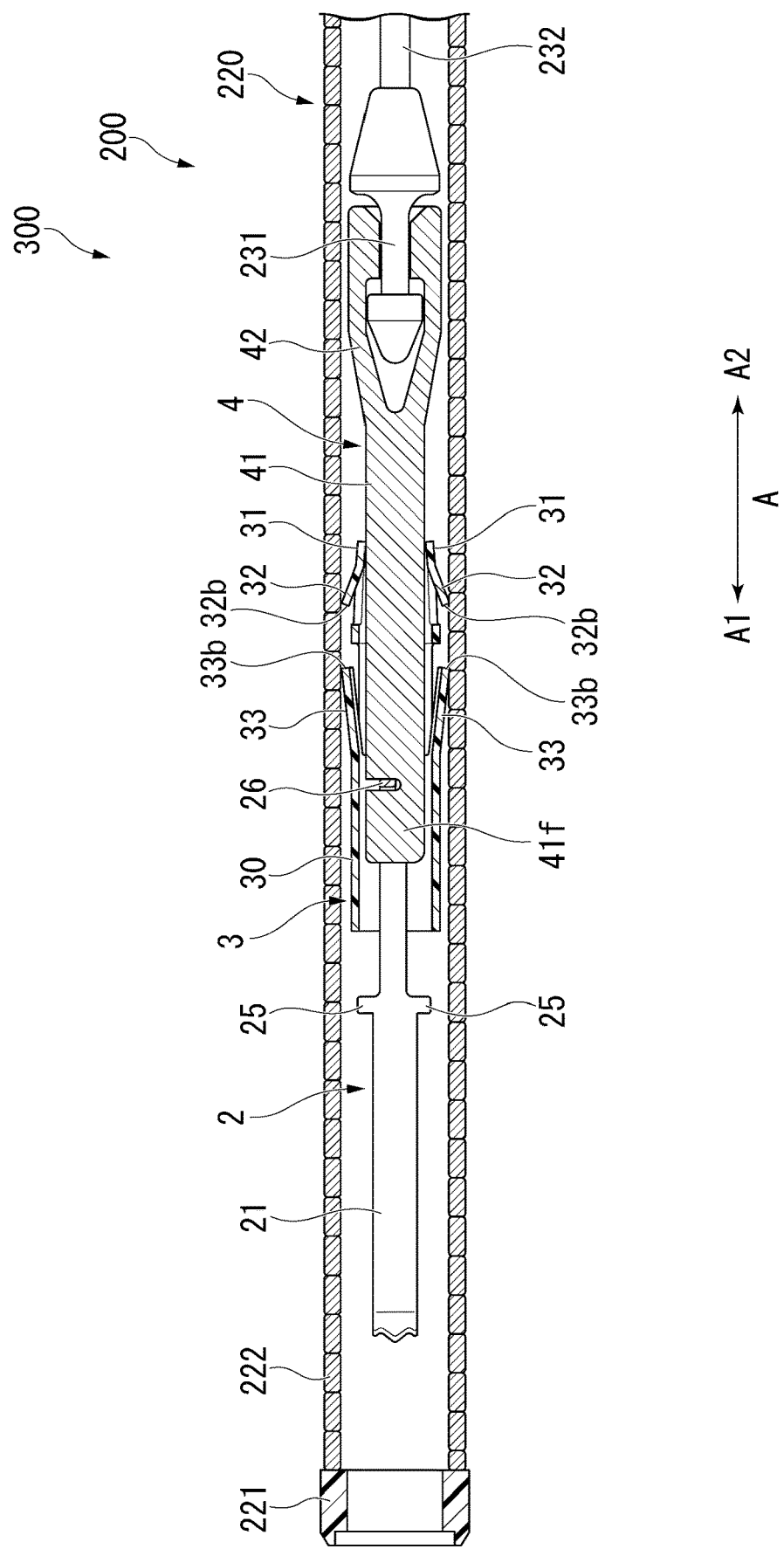
FIG. 6 is a cross-sectional view showing the clip unit that is accommodated into the sheath.

FIG. 6 is a cross-sectional view showing the clip unit 1 that is accommodated in the sheath 220.

The clip unit 1 is accommodated in the sheath 220 using the cartridge disclosed in PCT International Publication No. WO 2021/171407, for example. The user uses the cartridge to press the second wing 32 that is supported by the first wing 31 to the inside in the radial direction R while accommodating part at the proximal-end side A2 of the tubular member 3 in the sheath 220 (first accommodation step). Subsequently, the user uses the cartridge to press the second wing 32 to the inside in the radial direction R while accommodating the entire tubular member 3 in the sheath 220 (second accommodation step).

The second free end 32b of the second wing is pressed to the inside in the radial direction R by the sheath 220; however, the second free end 32b is still arranged in the outside region 39. The distance in the radial direction R from the central axis O1 to the second free end 32b is longer than the distance from the central axis O1 to the inner circumferential edge portion 225 provided in the distal-end tip. The third free end 33b of the third wing 33 is pressed to the inside in the radial direction R by the sheath 220.

The user introduces the clip 1 loaded in the clip introduction device 200 to the inside of the body via the channel of the endoscope.

Figure 7:
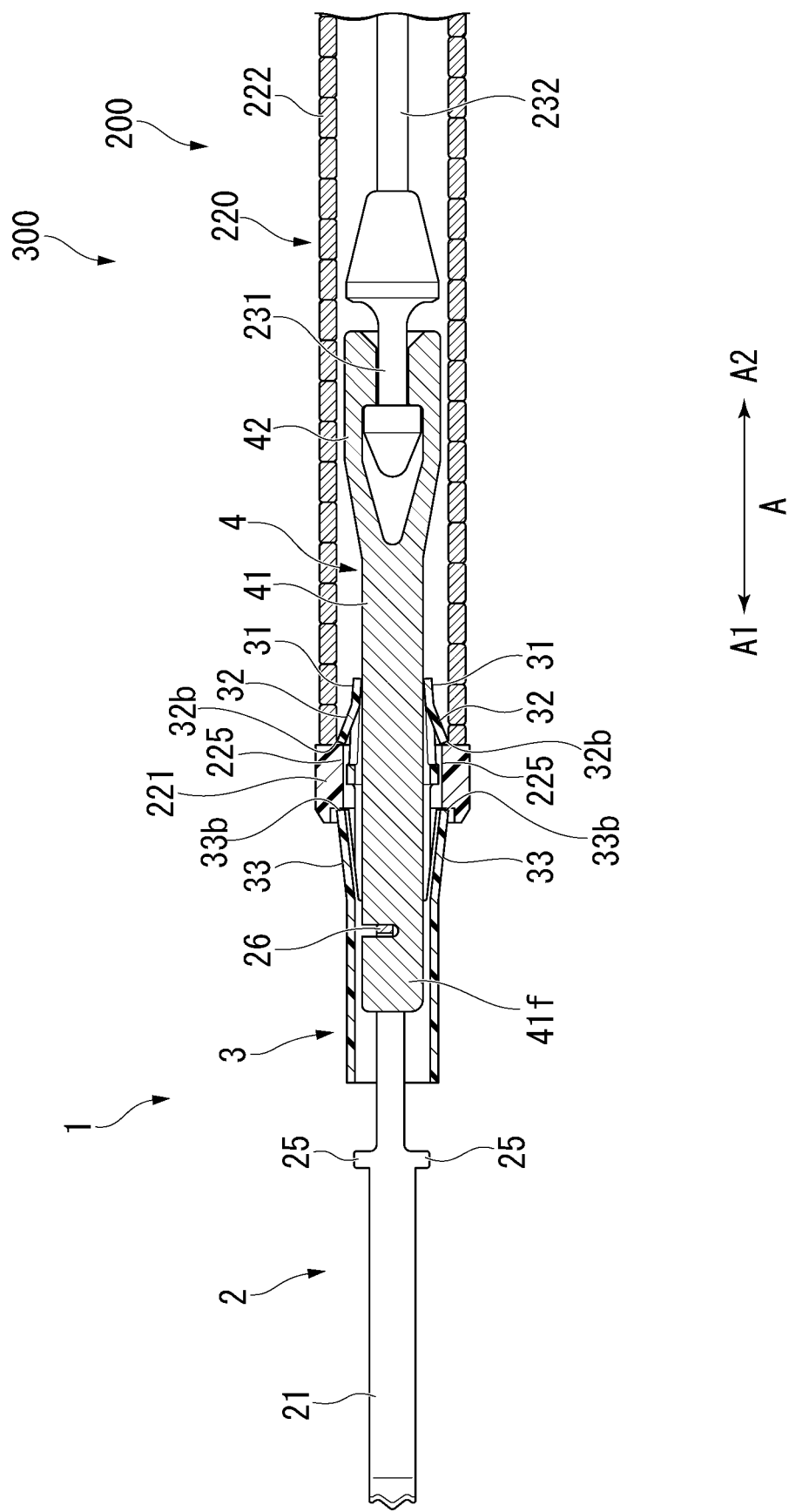
FIG. 7 is a cross-sectional view showing a grasping operation of the clip.

FIG. 7 is a cross-sectional view showing the grasping operations by the clip 2.

The user operates the operation portion 240 to advance the operation wire 230 so as to protrude part of the clip unit 1 from the distal-end tip 221 toward the distal-end side A1. More specifically, the user advances the clip unit 1 until the third wing 33 protrudes toward the distal-end side A1 from the distal-end tip 221. When the third free end 33b of the third wing protrudes toward the distal-end side A1 from the distal-end tip 221, the third free end 33b moves outwardly in the radial direction to return to the initial position.

The second free end 32b of the second wing 32 and the third free end 33b of the third wing 33 clamps the inner circumferential edge portion 225 of the distal-end tip 221 from the front and the rear in the longitudinal direction A (fixing step). As a result, the pressing tube 3 is fixed with respect to the distal-end tip 221. The second free end 32b of the second wing 32 and the third free end 33b of the third wing 33 may be movable until the outer region 39 until they are fully engaged with the inner circumferential edge portion 225. It is noted that the pressing tube 3 only has to be fixed such that the pressing tube 3 does not separate from the distal-end tip 221. For example, the second free end 32b of the second wing 32 and the third free end 33b of the third wing 33 may not simultaneously in contact with the inner circumferential edge portion 225.

The user operates the operation portion 240 to advance and retract the operation wire 230 so as to advance and retract the clip 2 in the state of fixing the pressing tube 3 with respect to the distal-end tip 221. The user retracts the slider 242 along the operation portion main body 241 to retract the clip 2 (traction step). By pulling the proximal-end portion 26 of the clip 2 to the proximal-end side A2, the pair of arms 21 are retracted into the pressing tube 3 and the pair of arms 21 are gradually closed. The user closes the pair of arms 21 so as to grasp the tissue by the pair of arms 21.

Figure 8:
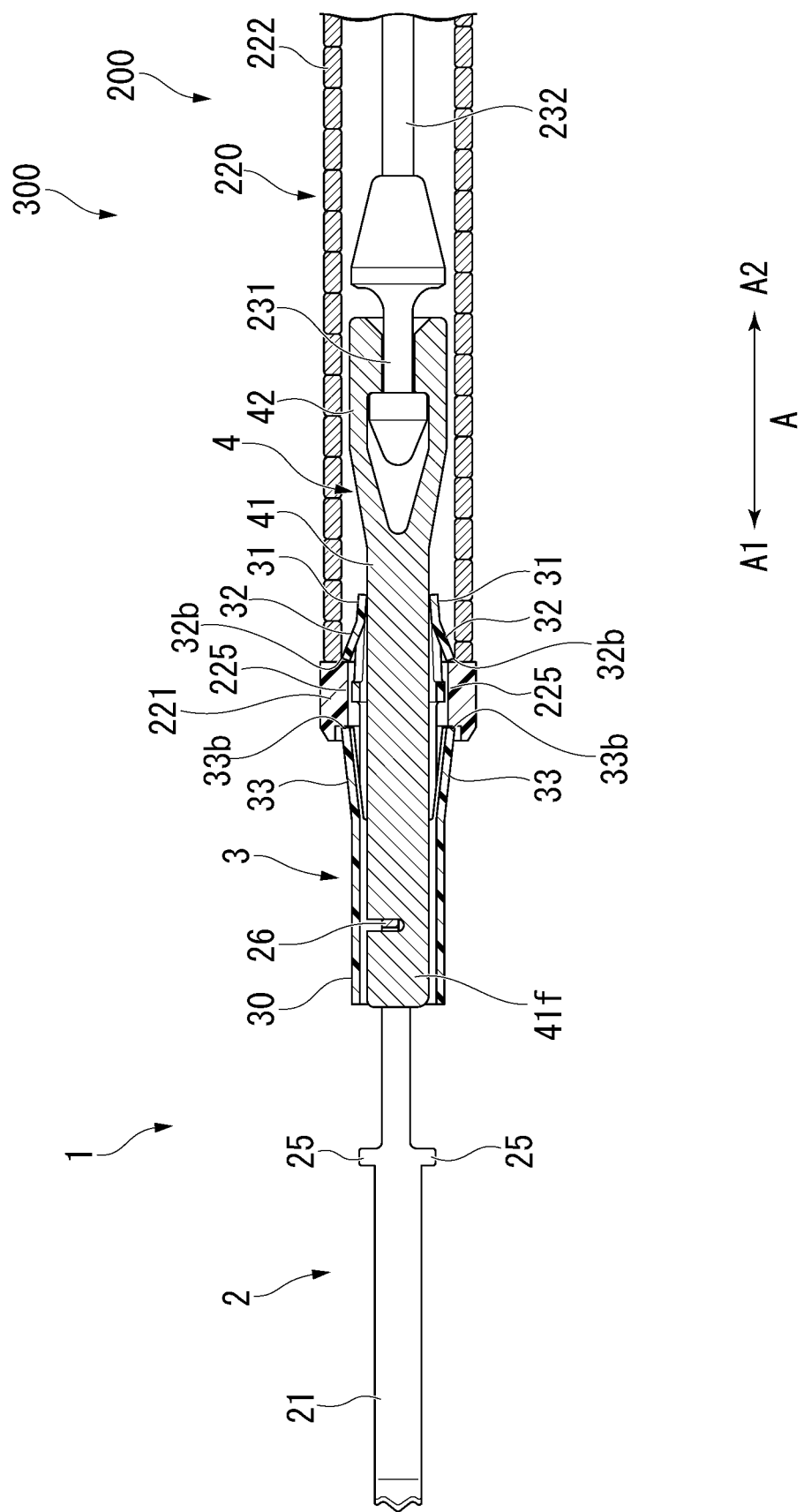
FIG. 8 is a cross-sectional view showing a re-grasping operation of the clip.

FIG. 8 is a cross-sectional view showing the re-grasping operations by the clip 2.

When the user advances the slider 242 along the operation portion main body 241 in this state, the clip 2 moves to the distal-end side A1. The proximal-end portion 26 of the clip 2 is pressed to the distal-end side A1 such that the pair of arms 21 are pressed outside from the pressing tube 3 and the pair of arms 21 are gradually opened. It is possible for the user to return the pair of arms 21 to the open state to re-grasp the tissue. The pressing tube 3 is fixed with respect to the distal-end tip 221 such that it is possible for the user to advance and retract the clip 2 only and it is easy to re-grasp the tissue.

Figure 9:
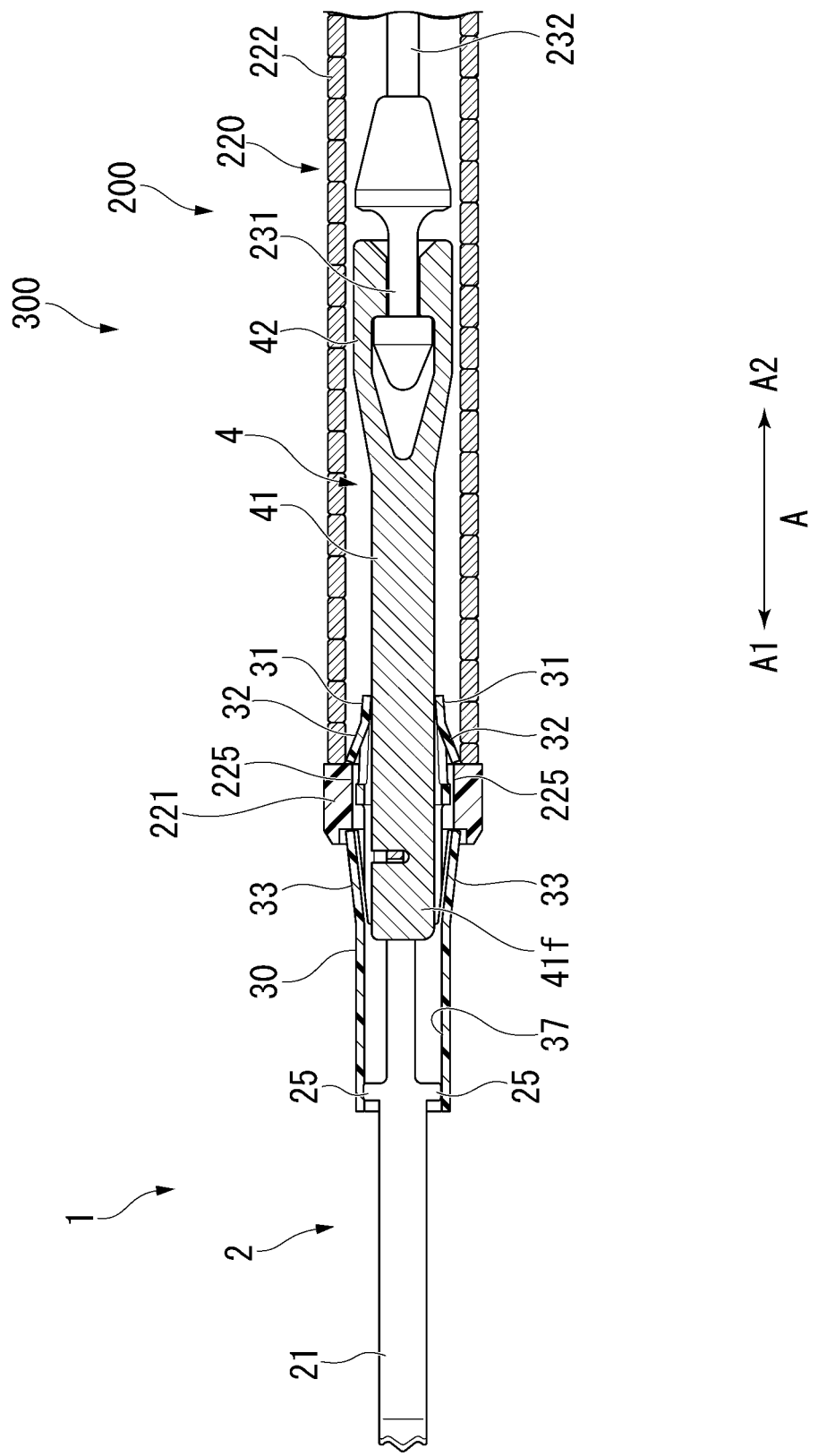
FIG. 9 is a cross-sectional view showing the clip unit where the clip is locked.

FIG. 9 is a cross-sectional view showing the clip unit 1 where the clip 2 is locked.

By further pulling the proximal-end portion 26 toward the proximal-end side A2, the engaging portion 25 is retracted into the internal space of the pressing tube 3. When the engaging portion 25 is retracted into the internal space of the pressing tube 3, the engaging portion 25 and the inner circumferential surface 37 of the pressing tube 3 are engaged with each other. As a result, the movement of the clip 2 toward the distal-end side A1 with respect to the pressing tube 3 is restricted and the pair of arms 21 are locked in the closed state. When the pair of arms 21 are locked in the closed state, it is impossible for the pair of arms 21 to return to the open state. It is noted that the pressing tube 3 may include a convex portion that is engageable with the engaging portion 25 on the inner circumferential surface 37. It is possible for the pressing tube 3 to definitely lock the pair of arms 21 in the closed state by engaging the convex portion with the engaging portion 25.

Figure 10:
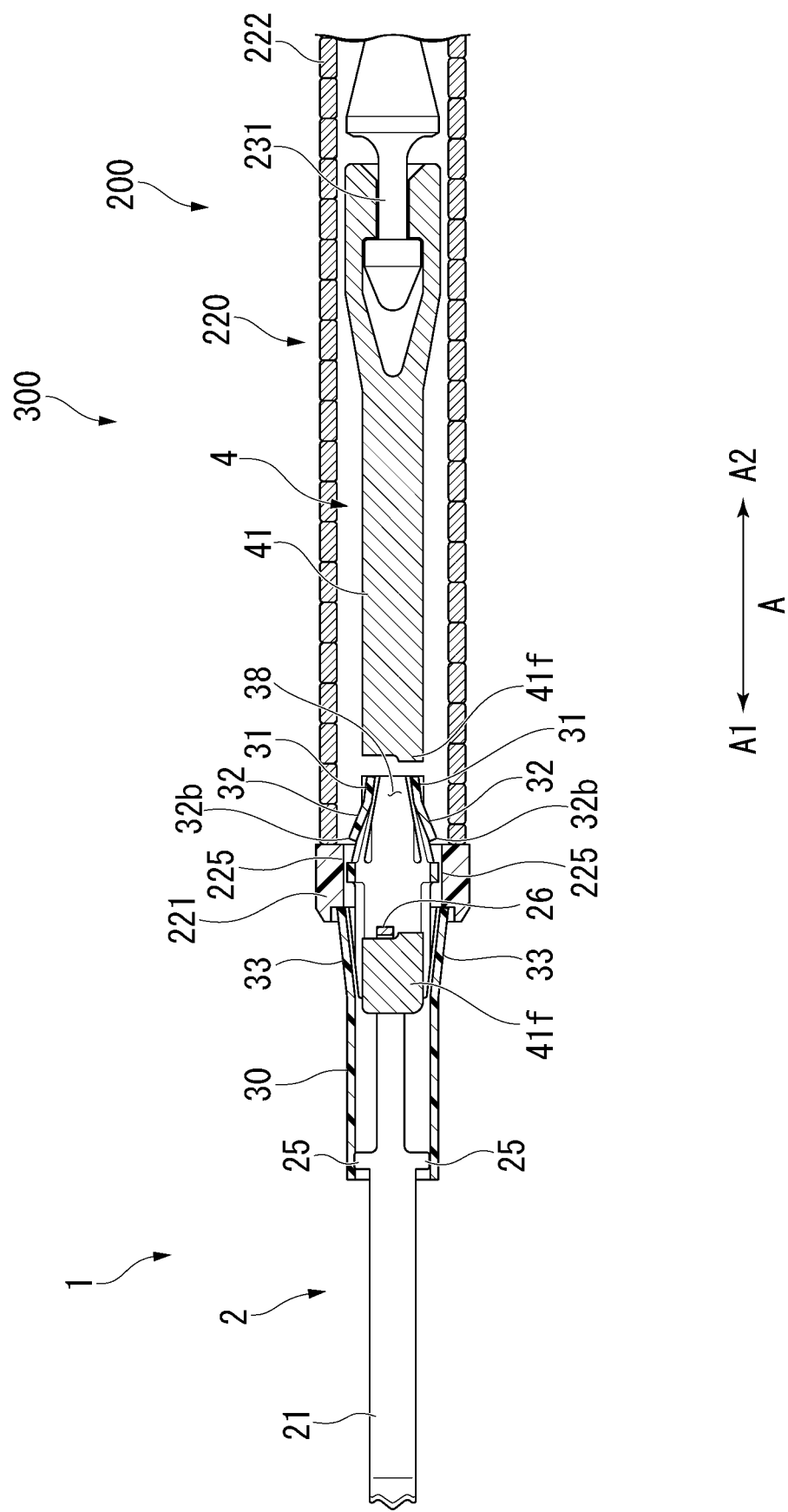
FIG. 10 is a cross-sectional view showing the clip unit from which the connection member is separated.

FIG. 10 is a cross-sectional view showing the clip unit 1 where the connection member 4 is separated.

The user further pulls the clip 2. The engaging portion 25 and the inner circumferential surface 37 of the pressing tube 3 are engaged with each other and the pair of arms 21 are locked in the closed state such that the clip 2 is not further pulled toward the proximal-end side A2. In this state, when the user further pulls the clip 2, the predetermined breaking force is applied to the hook 41f and the hook 41 is broken. As a result, the clip 2 and the connection member 4 are separated. It is noted that the clip 2 and the connection member 4 may be separated from each other since the hook 41 is deformed. Also, the pair of arms 21 may include a stopper configured to prevent the pair of arms 21 from being further pulled toward the proximal-end side A2 with respect to the pressing tube 3 at the time of being locked in the closed state. For example, the stopper is a convex portion provided at the distal-end side A1 with respect to the engaging portion 25 that is impossible to enter the internal space of the pressing tube 3. The stopper is engaged with the pressing tube 3 such that the clip 2 is not pulled toward the proximal-end side A2 and it is easy for the connection member 4 to be separated from the clip 2.

The user operates the operation portion 240 to retract the operation wire 230 so as to pull out the connection member 4 from the pressing tube 3. The first wing 31 and the connection member 4 separates from each other to not to be in contact with each other. The first wing 31 moves until the inner region 38 as the initial position. The second wing 32 moves until the inner region 38 as the initial position since the first wing 31 returns to the initial position. The first wing 31 and the second wing 32 move until the inner region 38 such that the first wing 31 and the second wing 32 can pass through the inner circumferential edge portion 225 of the distal-end tip 221 toward the distal-end side A1. In other words, the pressing tube 3 is movable to the distal-end side A1 with respect to the inner circumferential edge portion 225 of the distal-end tip 221. As a result, the fixation of the pressing tube 3 with respect to the distal-end tip 221 is released (release step).

The user retracts the sheath 220 to indwell the clip 2 and the pressing tube 3 in the state of ligating the tissue inside the body (indwelling step).

According to the clip delivery device 300 and the clip introduction device 200 according to the present embodiment, it is possible to deliver the clip unit 1 in the state of accommodating the clip unit 1 in the sheath 220 through the channel of the endoscope.

According to the clip delivery device 300 and the clip introduction device 200 according to the present embodiment, it is possible to reload the clip unit 1 into the clip introduction device 200 (reloadable) and it is possible for the clip 2 of the clip unit 1 to re-grasp the tissue (re-opening) such that the loading and the separation of the clip unit 1 with respect to the clip introduction device 200 can be definitely performed.

As described above, the first embodiment of the present disclosure has been described in detail with reference to the drawings; however, the specific configuration is not limited to the present embodiment, and design changes and the like are included within the scope of the present disclosure. Also, the configurational elements shown in the present embodiment and the modification examples shown below can be combined as appropriate.

Modification Example 1

Figure 11:
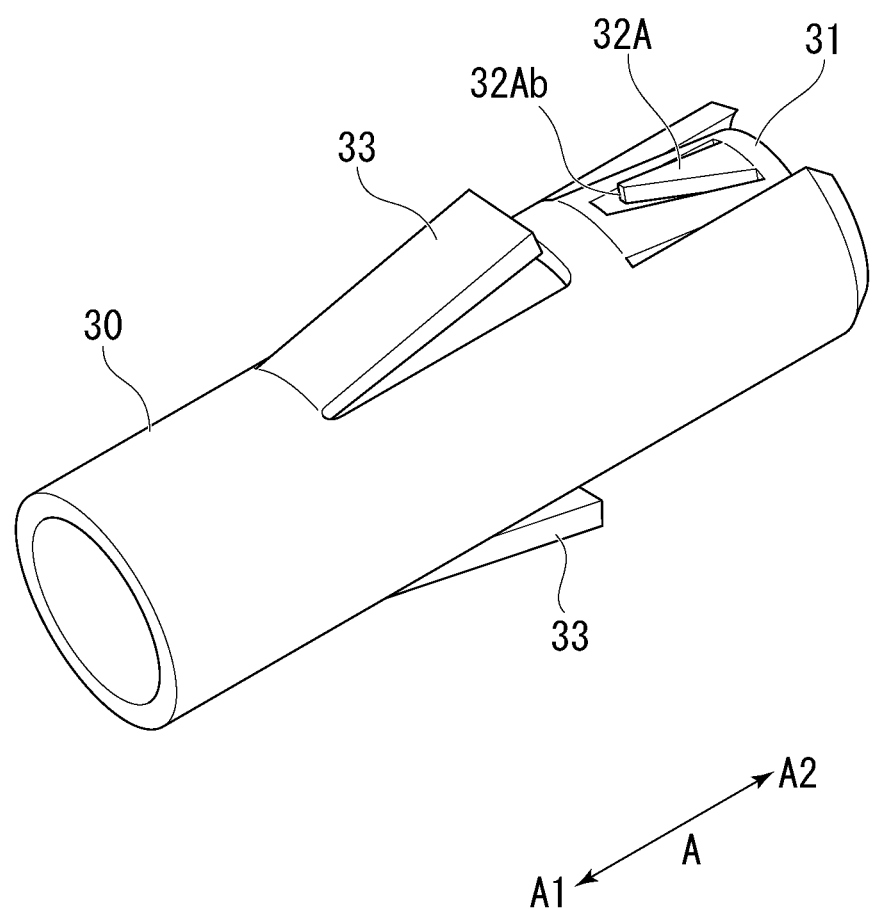
FIG. 11 is a view showing a modification example of a second wing of the pressing tube.

In the above-described embodiment, the second wing 32 is formed in the rectangle shape when viewed from the radial direction R. However, the shape of the second wing 32 is not limited to this configuration. FIG. 11 is a view showing a second wing 32A as a modification example of the second wing 32. The second wing 32A is formed in a triangle shape when viewed from the radial direction R. A second free end (end portion at the distal-end side) 32Ab is thinner when compared with the second free end 32b of the second wing 32. Accordingly, the strain in the second wing 32A is dispersed and the second wing 32A is less likely to be plastically deformed. Also, the rigidity at the first free end side in the first wing 31 is decreased such that the strain in the first wing 31 is also dispersed.

Modification Example 2

Figure 12:
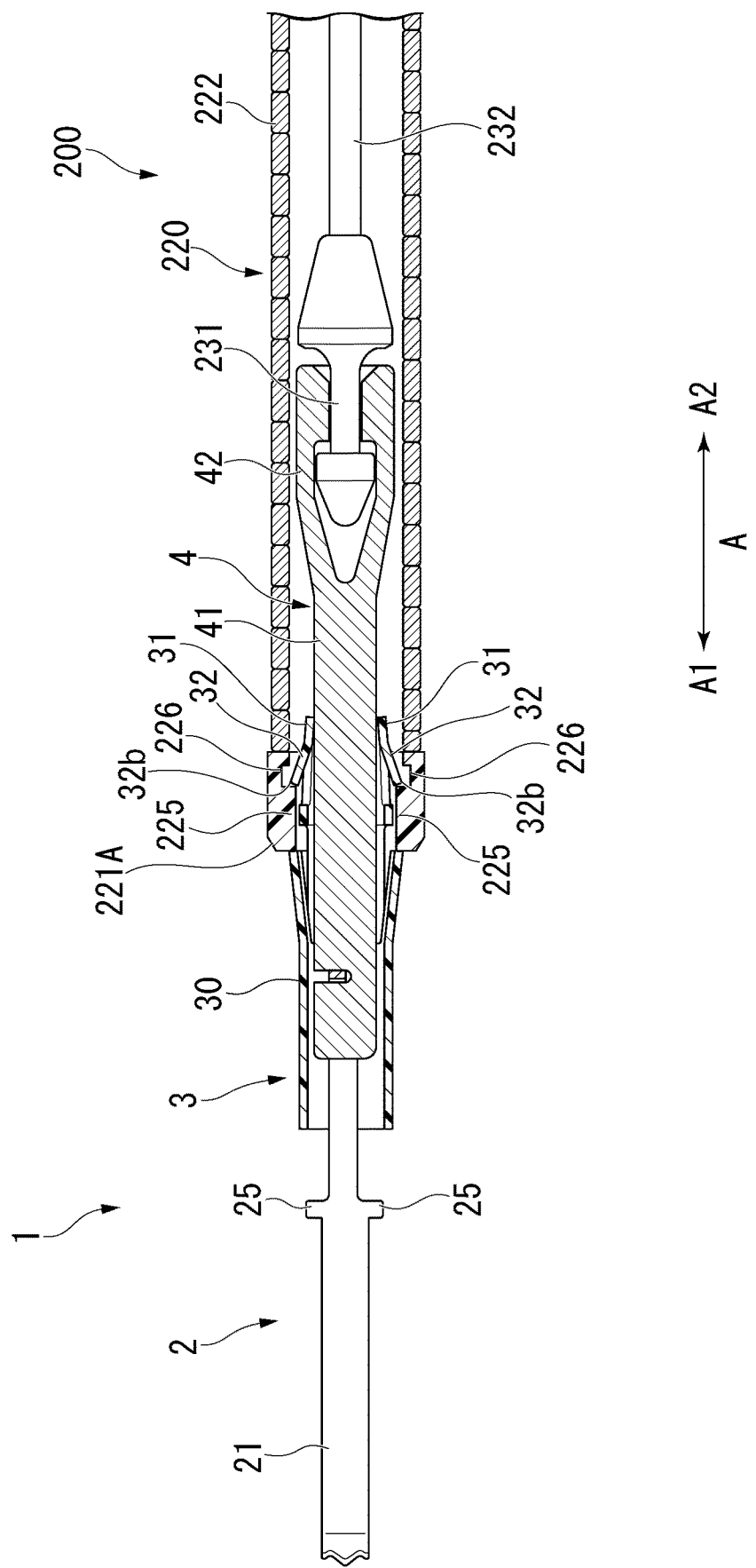
FIG. 12 is a view showing a modification example of a distal-end tip of the clip introduction device.

FIG. 12 is a view showing a distal-end tip 221A as a modification example of the distal-end tip 221. The distal-end tip 221A includes a concave portion 226 that is recessed toward the outside in the radial direction R at the proximal-end side A2 of the inner circumferential edge portion 225. The second free end 32b of the second wing 32 is fitted into the concave portion 226. Also, the protrusion length of the convex portion protruding toward the inside in the radial direction R on the inner surface of the distal-end tip 221A may be set to be smaller when compared with the above-described embodiment such that it is difficult for the clip 2 to be caught by the inner edge of the distal-end tip 221A when passing through the distal-end tip 221A.

Second Embodiment

A second embodiment of the present disclosure will be described by referring from FIG. 13 to FIG. 15. In the following description, the described configurations and the common configurations will be designated with the same reference signs and the duplicate description will be omitted. The first wing 31 and the second wing 32 in the clip delivery device according to the second embodiment are different from that in the clip delivery device 300 according to the first embodiment.

The clip delivery device (clip system, clip device) according to the present embodiment includes the clip introduction device (applicator) 200 and a clip unit 1B.

The clip unit 1B includes the clip 2, a pressing tube 3B, and the connection member 4. The proximal-end side A2 of the clip 2 is inserted into the internal space of the pressing tube 3B.

Figure 13:
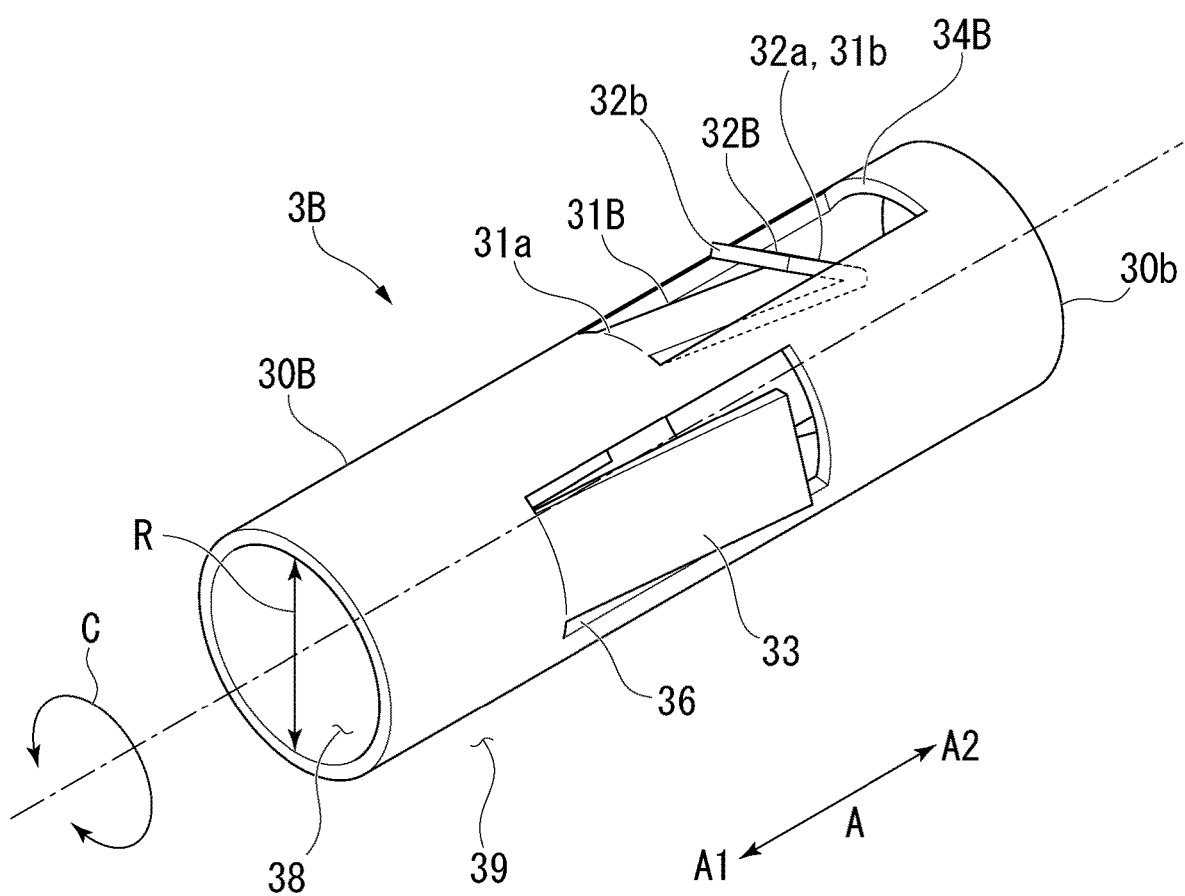
FIG. 13 is a perspective view showing a pressing tube of a clip delivery device according to a second embodiment.

FIG. 13 is a perspective view showing the pressing tube 3B.

The pressing tube (tubular member) 3B is a tubular member that is capable of accommodating at least part of the clip 2. The pressing tube 3B can fix the clip 2 in the closed state that is retracted into the internal space thereof. The pressing tube 3B includes a pressing tube main body 30B formed in a cylindrical shape, a first wing 31B, a second wing 32B, and a third wing 33.

The pressing tube main body (tubular member main body) 30B is the same member with the pressing tube main body 30 according to the first embodiment, and is different from the pressing tube main body 30 only in the first opening 34. A first opening 34B and a third opening 36 penetrating in the radial direction are formed in the pressing tube main body 30B. The first opening 34B is an opening that is not continuous to the proximal end 30b of the pressing tube main body 30B, and is provided on both sides thereof to sandwich the central axis O1. The first opening 34B and the third opening 36 are formed at different positions in the circumferential direction C of the pressing tube main body 30B.

The first wing 31B is supported by the pressing tube main body 30B to be elastically deformable in the radial direction R, and is biased to be disposed in the inner region 38 of the pressing tube main body 30B in the state in which there is no external force applied. Two of first wings 31B are provided in the pressing tube main body 30B on both sides to sandwich the central axis O1. The first wing 31B is formed in the rectangle shape when viewed from the radial direction R.

The first wing 31B is supported by the pressing tube main body 30B at the distal-end side A1. More specifically, the first fixed end 31a at the distal-end side A1 of the first wing 31B is supported by the pressing tube main body 30B. The first free end 31b at the proximal-end side A2 of the first wing 31B is elastically deformable in the radial direction R. The first wing 31B is disposed at the position overlapping the first opening 34B when viewed from the radial direction R, and the first wing 31B does not come into contact with the pressing tube main body 30B even in the case of being elastically deformed in the radial direction R.

The second wing 32B is supported by the first wing 31B to be elastically deformable in the radial direction R, and is biased to be arranged on the outside in the radial direction R of the first wing 31B in the state where no external force is applied thereto. The two first wings 31B support the second wings 32B respectively and the two second wings 32B are provided on both sides of the central axis O1 to sandwich the central axis O1. The second wing 32B is formed in a rectangle shape when viewed in the radial direction R.

The second wing 32B is supported by the first wing 31B on the proximal-end side A2. Specifically, the second fixed end 32a on the proximal-end side A2 of the second wing 32B is supported by the first free end (end portion at the proximal-end side) 31b of the first wing 31B. The second free end (end portion at the distal-end side) 32b on the distal-end side A1 of the second wing 32B is elastically deformable in the radial direction R. The second wing 32B is disposed at the position overlapping the first wing 31B when viewed in the radial direction R.

When the first wing 31B is disposed in the inner region 38 in the state in which no external force is received, the second free end 32b of the second wing 32B is disposed in the inner region 38.

The third wing 33 is disposed at the distal-end side A1 with respect to the second wing 32B. In the present embodiment, the first wing 31B and the third wing 33 are formed at different positions in the circumferential direction C of the pressing tube main body 30B, and the length of the pressing tube 3B in the longitudinal direction A may be shorter than that of the pressing tube 3 according to the first embodiment.

Figure 14:
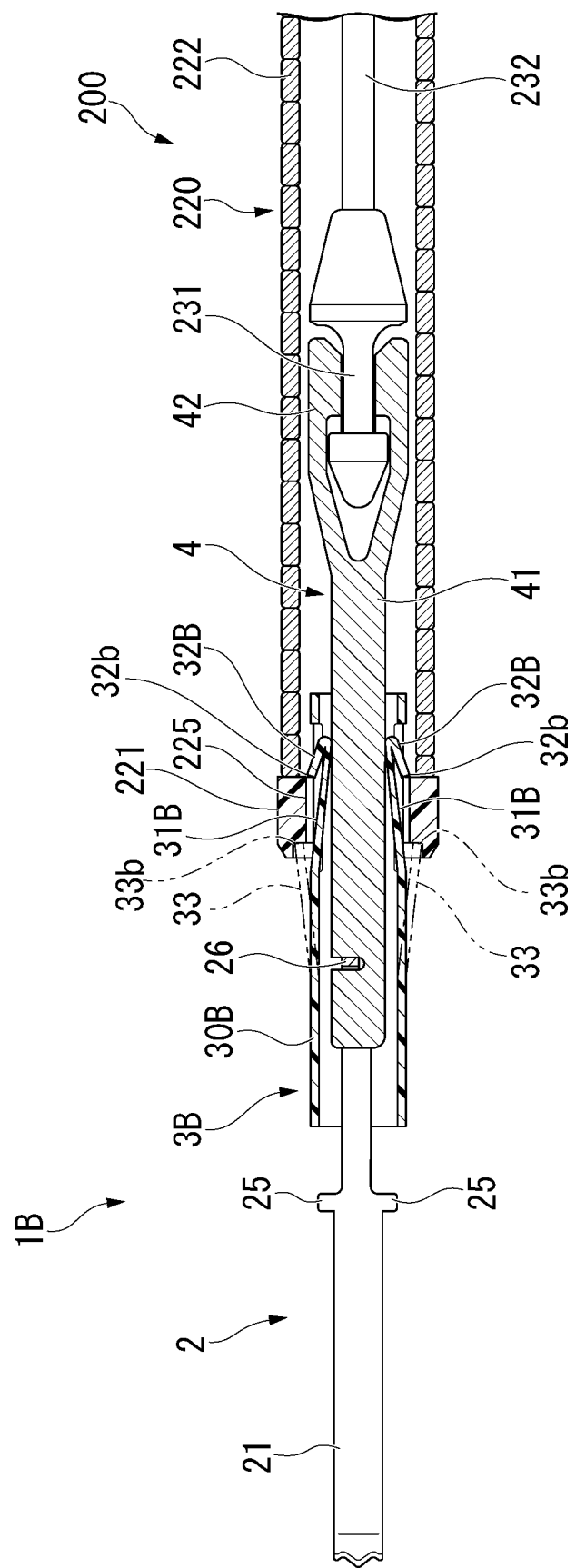
FIG. 14 is a cross-sectional view showing the clip unit to which the pressing tube is fixed.

FIG. 14 is a cross-sectional view showing the clip unit 1B to which the pressing tube 3B is fixed.

The second free end 32b of the second wing 32B and the third free end 33b of the third wing 33 clamp the inner circumferential edge portion 225 of the distal-end tip 221 from the front and the rear in the longitudinal direction (fixing step). As a result, the pressing tube 3B is fixed with respect to the distal-end tip 221.

Figure 15:
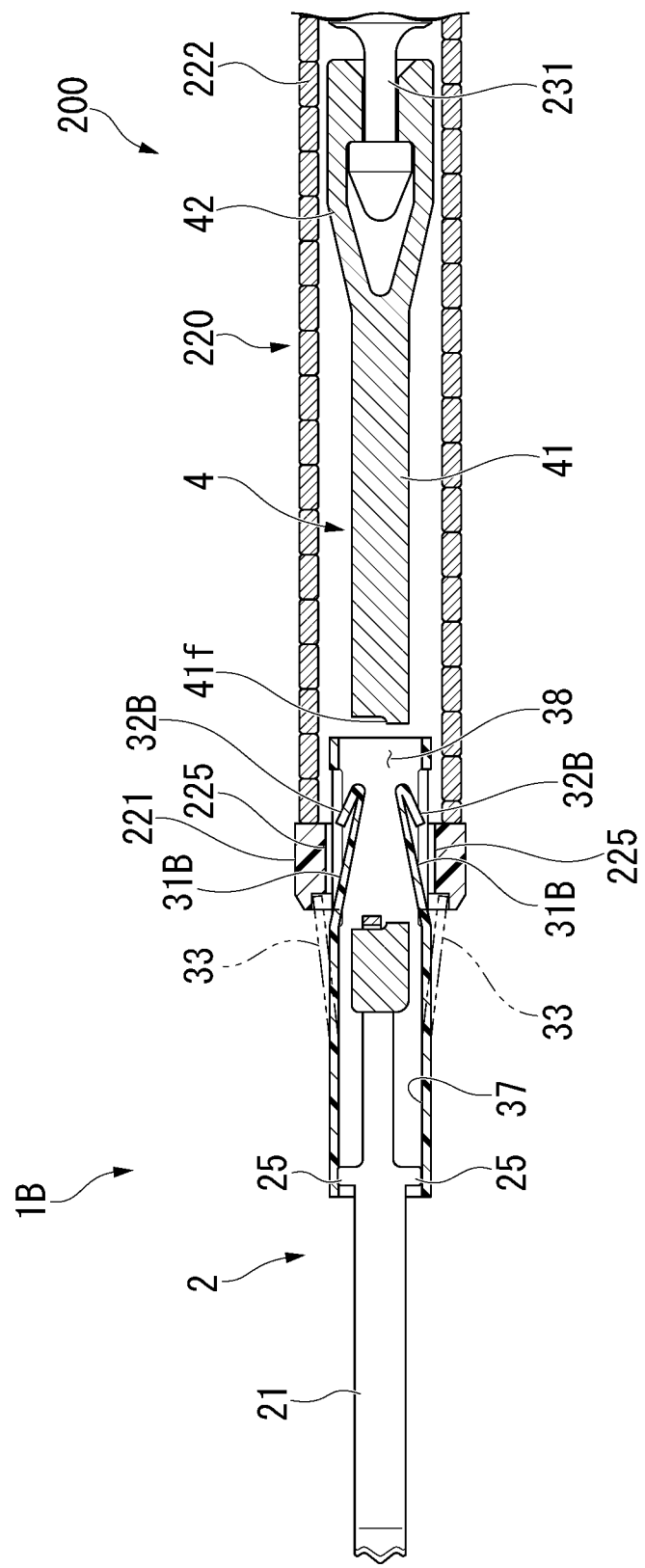
FIG. 15 is a cross-sectional view showing the clip unit from which the connection member is separated.

FIG. 15 is a cross-sectional view showing the clip unit 1B from which the connection member 4 is separated.

The user operates the operation portion 240 to retract the operation wire 230 so as to pull out the connection member 4 from the pressing tube 3B. The first wing 31B and the connection member 4 separates from each other to not to be in contact with each other. The first wing 31B moves until the inner region 38 as the initial position. The second wing 32B moves until the inner region 38 as the initial position since the first wing 31B returns to the initial position. The first wing 31B and the second wing 32B move until the inner region 38 such that the first wing 31B and the second wing 32B can pass through the inner circumferential edge portion 225 of the distal-end tip 221 toward the distal-end side A1. In other words, the pressing tube 3B is movable to the distal-end side A1 with respect to the inner circumferential edge portion 225 of the distal-end tip 221. As a result, the fixation of the pressing tube 3B with respect to the distal-end tip 221 is released (release step).

According to the clip delivery device and the clip introduction device 200B according to the present embodiment, it is possible to deliver the clip unit 1B in the state of accommodating the clip unit 1B in the sheath 220 through the channel of the endoscope.

According to the clip delivery device and the clip introduction device 200B according to the present embodiment, it is possible to reload the clip unit 1B into the clip introduction device 200B (reloadable) and it is possible for the clip 2 of the clip unit 1B to re-grasp the tissue (re-opening) such that the loading and the separation of the clip unit 1B with respect to the clip introduction device 200B can be definitely performed.

As described above, the second embodiment of the present disclosure has been described in detail with reference to the drawings; however, the specific configuration is not limited to the present embodiment, and design changes and the like are included within the scope of the present disclosure. Also, the configurational elements shown in the present embodiment and the modification examples shown below can be combined as appropriate.

Modification Example 3

Figure 16:
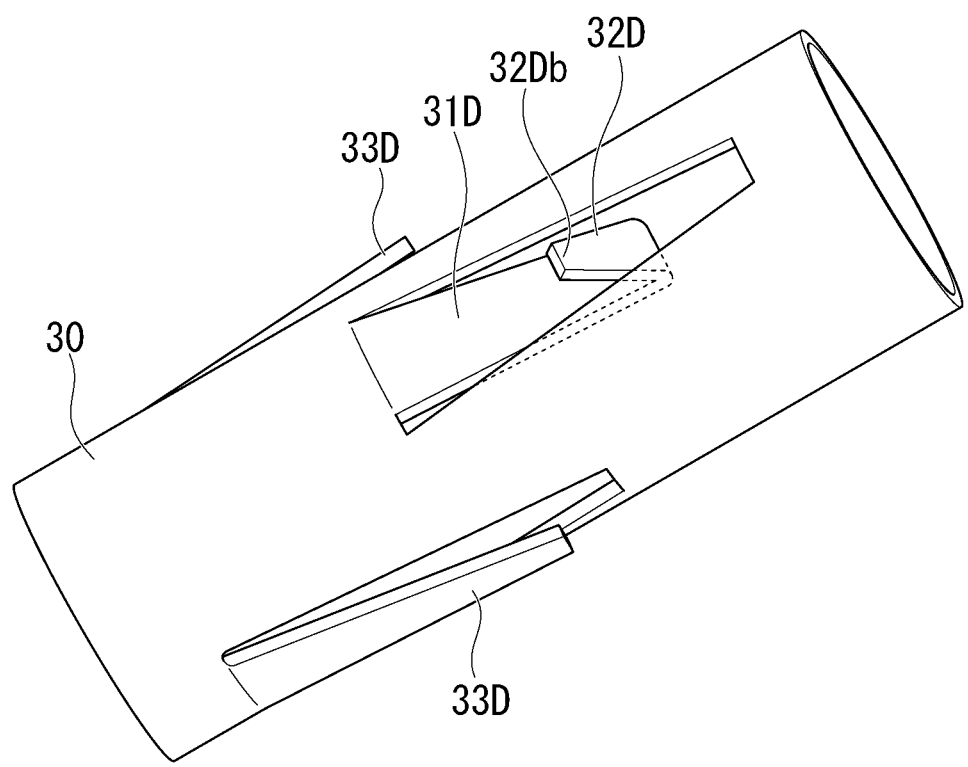
FIG. 16 is a view showing modification examples of the first wing, the second wing, and the third wing of the pressing tube.

In the above-described embodiment, the first wing 31B, the second wing 32B, and the third wing 33 are formed in the rectangle shape when viewed from the radial direction R. However, the shape of the first wing 31B, the second wing 32B, and the third wing 33 is not limited to this configuration. FIG. 16 is a view showing a first wing 31D, a second wing 32D, and a third wing 33D as the modification examples of the first wing 31B, the second wing 32B, and the third wing 33. The first wing 31D and the second wing 32D are formed by folding a portion formed in the triangle shape when viewed from the radial direction R in the longitudinal direction A. The third wing 33D is formed in a triangle shape when viewed from the radial direction R. A second free end (end portion at the distal-end side) 32Db is thinner when compared with the second free end 32b of the second wing 32. Accordingly, the strain in the second wing 32D is dispersed and the second wing 32D is less likely to be plastically deformed. Also, the rigidity at the first free end side in the first wing 31D is decreased such that the strain in the first wing 31D is also dispersed.

Third Embodiment

A third embodiment of the present disclosure will be described with references from FIG. 17 to FIG. 19. In the following description, the described configurations and the common configurations will be designated with the same reference signs and the duplicate description will be omitted. The clip delivery device according to the third embodiment is different in the first wing 31 and the second wing 32 when compared with the clip delivery device 300 according to the first embodiment.

The clip delivery device (clip system, clip device) according to the present embodiment includes the clip introduction device (applicator) 200 and a clip unit 1C.

The clip unit 1C includes the clip 2, a pressing tube 3C, and the connection member 4. The proximal-end side A2 of the clip 2 is inserted into the internal space of the pressing tube 3C.

Figure 17:
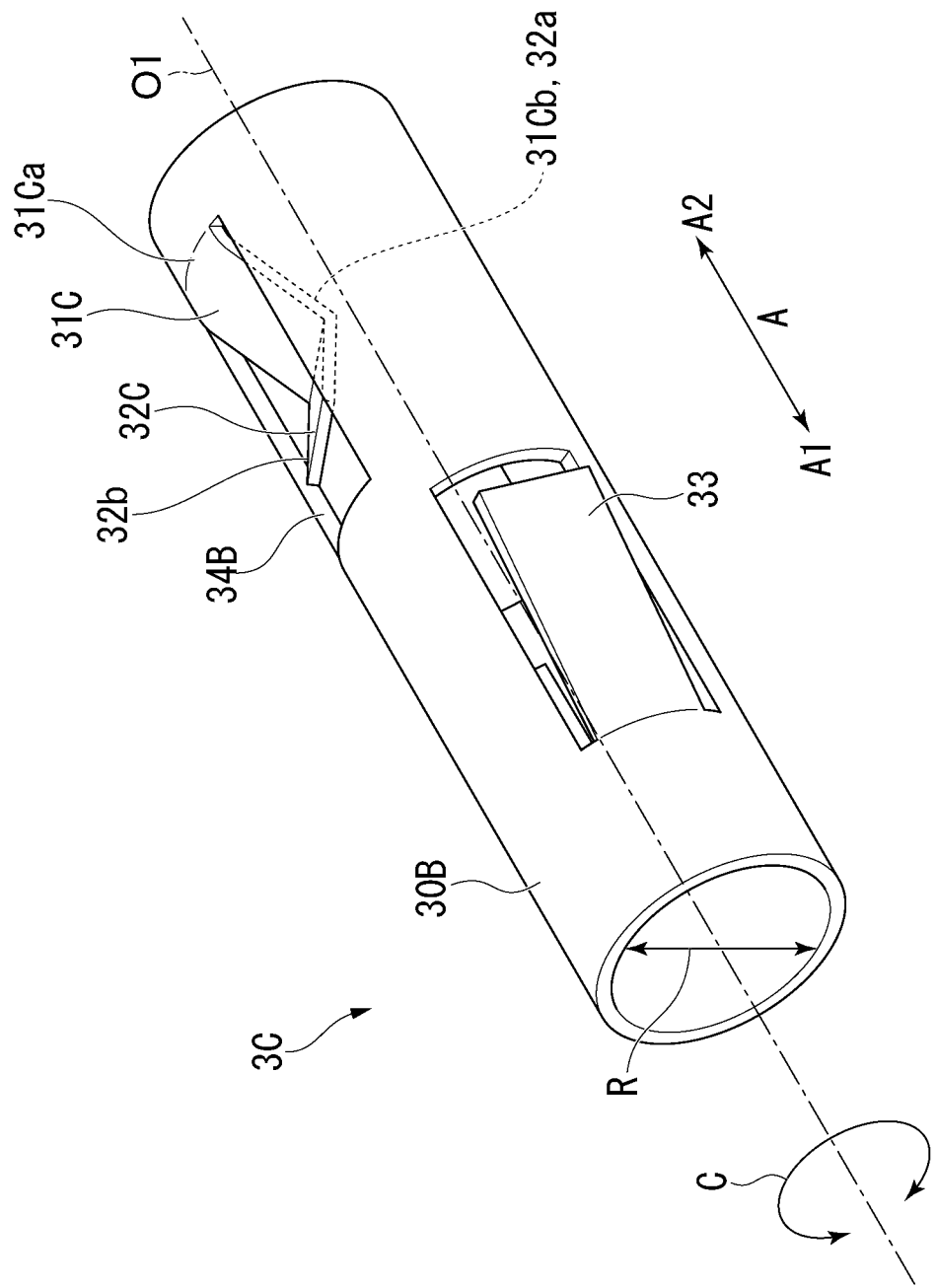
FIG. 17 is a perspective view showing a pressing tube of a clip delivery device according to a third embodiment.

FIG. 17 is a perspective view showing the pressing tube 3C.

The pressing tube (tubular member) 3C is a tubular member that is capable of accommodating at least part of the clip 2. The pressing tube 3C can fix the clip 2 in the closed state that is retracted into the internal space thereof. The pressing tube 3C includes the pressing tube main body 30B formed in the cylindrical shape, a first wing 31C, a second wing 32C, and the third wing 33.

The first wing 31C is supported by the pressing tube main body 30B to be elastically deformable in the radial direction R, and is biased to be disposed in the inner region 38 of the pressing tube main body 30B in the state in which there is no external force applied. Two of first wings 31C are provided in the pressing tube main body 30B on both sides to sandwich the central axis O1. The first wing 31C is formed in the rectangle shape when viewed from the radial direction R.

The first wing 31C is supported by the pressing tube main body 30B at the proximal-end side A2. More specifically, the first fixed end 31Ca at the proximal-end side A2 of the first wing 31C is supported by the pressing tube main body 30B. The first free end 31Cb at the distal-end side A1 of the first wing 31C is elastically deformable in the radial direction R. The first wing 31C is disposed at the position overlapping the first opening 34B when viewed from the radial direction R, and the first wing 31C does not come into contact with the pressing tube main body 30B even in the case of being elastically deformed in the radial direction R.

The second wing 32C is supported by the first wing 31C to be elastically deformable in the radial direction R, and is biased to be arranged on the outside in the radial direction R of the first wing 31C in the state where no external force is applied thereto. The two first wings 31C support the second wings 32C respectively and the two second wings 32C are provided on both sides of the central axis O1 to sandwich the central axis O1. The second wing 32C is formed in the rectangle shape when viewed in the radial direction R.

The second wing 32C is supported by the first wing 31C on the proximal-end side A2. Specifically, the second fixed end 32a on the proximal-end side A2 of the second wing 32C is supported by the first free end (end portion at the distal-end side) 31Cb of the first wing 31C. The second free end (end portion at the distal-end side) 32b at the distal-end side A1 of the second wing 32C is elastically deformable in the radial direction R. The second wing 32C is disposed at the position overlapping the first opening 34B when viewed in the radial direction R, and the second wing 32C is not in contact with the pressing tube main body 30B even in the case of being elastically deformed in the radial direction R.

When the first wing 31C is disposed in the inner region 38 in the state in which no external force is received, the second free end 32b of the second wing 32C is disposed in the inner region 38.

The third wing 33 is disposed at the distal-end side A1 with respect to the second wing 32C. In the present embodiment, the first wing 31C and the third wing 33 are formed at different positions in the circumferential direction C of the pressing tube main body 30B. Similar to the first embodiment, it is noted that the first wing 31C and the third wing 33 may be formed at the same position in the circumferential direction C of the pressing tube main body 30B.

Figure 18:
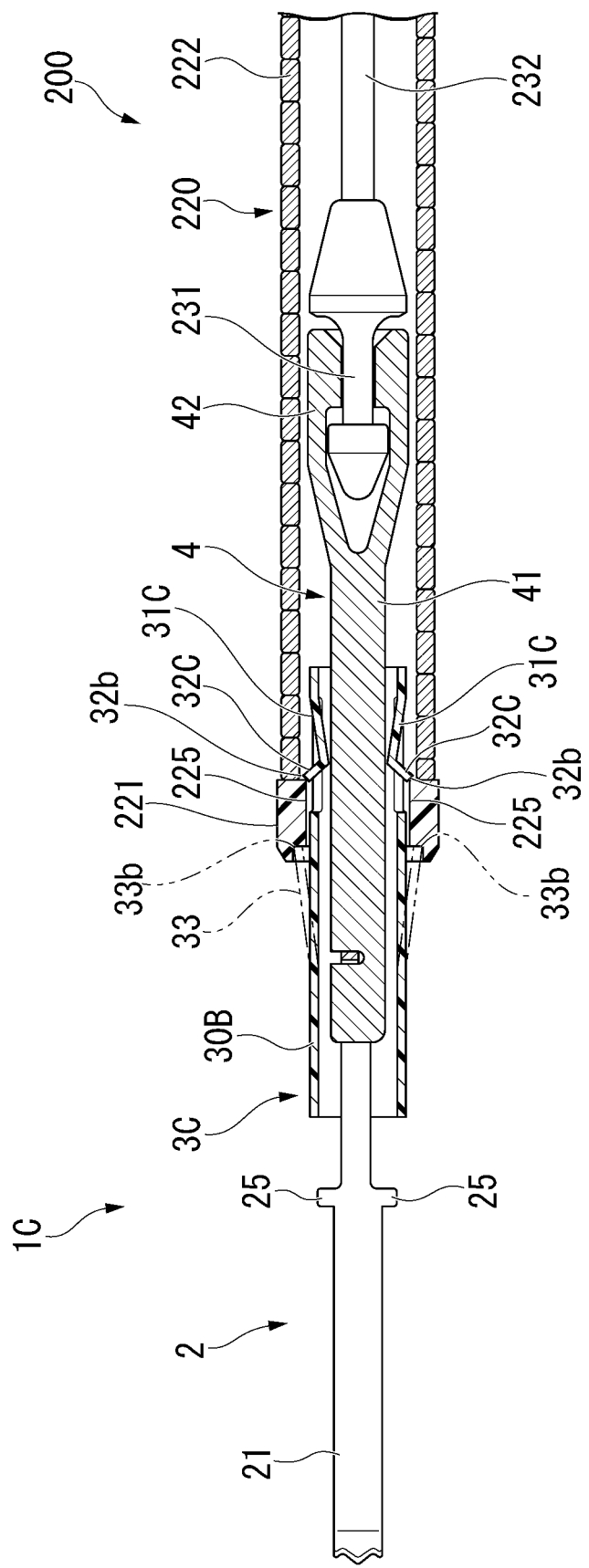
FIG. 18 is a cross-sectional view showing the clip unit to which the pressing tube is fixed.

FIG. 18 is a cross-sectional view showing the clip unit 1C to which the pressing tube 3C is fixed.

The second free end 32b of the second wing 32C and the third free end 33b of the third wing 33 clamp the inner circumferential edge portion 225 of the distal-end tip 221 from the front and the rear in the longitudinal direction (fixing step). As a result, the pressing tube 3C is fixed with respect to the distal-end tip 221.

Figure 19:
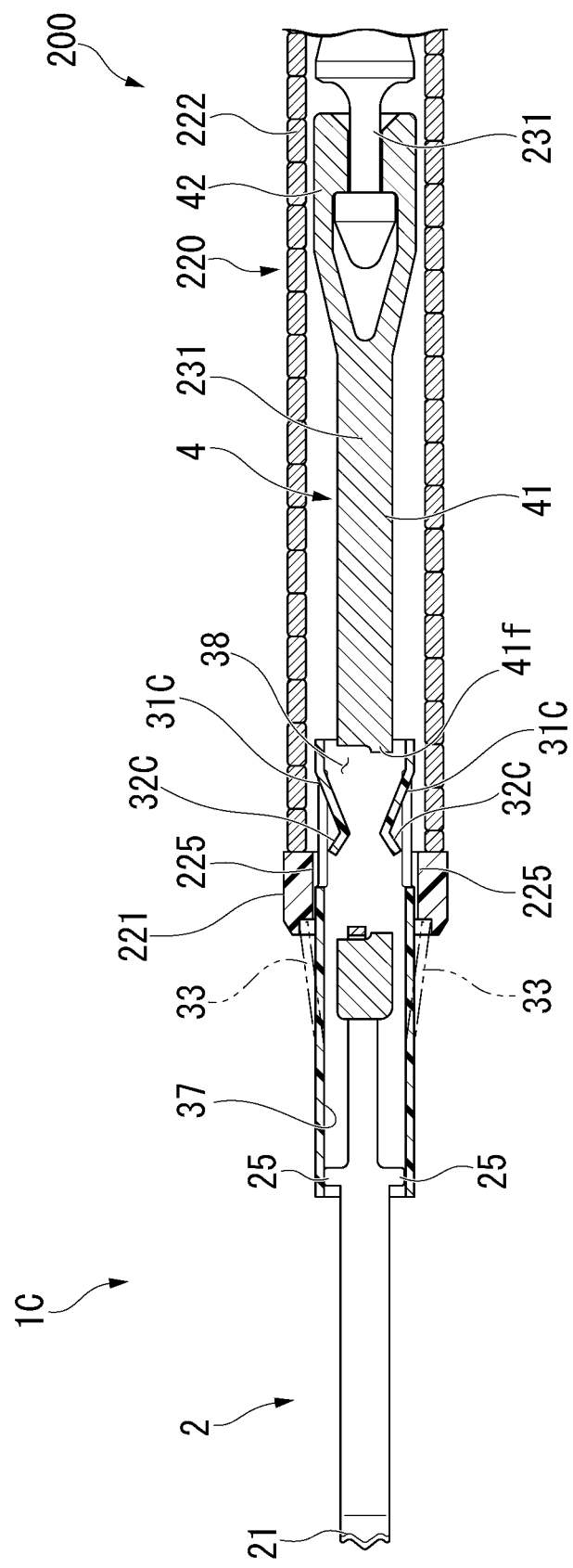
FIG. 19 is a cross-sectional view showing the clip unit from which the connection member is separated.

FIG. 19 is a cross-sectional view showing the clip unit 1C from which the connection member 4 is separated.

The user operates the operation portion 240 to retract the operation wire 230 so as to pull out the connection member 4 from the pressing tube 3C. The first wing 31C and the connection member 4 separates from each other to not to be in contact with each other. The first wing 31C moves until the inner region 38 as the initial position. The second wing 32C moves until the inner region 38 as the initial position since the first wing 31C returns to the initial position. The first wing 31C and the second wing 32C move until the inner region 38 such that the first wing 31C and the second wing 32C can pass through the inner circumferential edge portion 225 of the distal-end tip 221 toward the distal-end side A1. In other words, the pressing tube 3C is movable to the distal-end side A1 with respect to the inner circumferential edge portion 225 of the distal-end tip 221. As a result, the fixation of the pressing tube 3C with respect to the distal-end tip 221 is released (release step).

According to the clip delivery device and the clip introduction device 200 according to the present embodiment, it is possible to deliver the clip unit 1C in the state of accommodating the clip unit 1C in the sheath 220 through the channel of the endoscope.

According to the clip delivery device and the clip introduction device 200 according to the present embodiment, it is possible to reload the clip unit 1C into the clip introduction device 200B (reloadable) and it is possible for the clip 2 of the clip unit 1C to re-grasp the tissue (re-opening) such that the loading and the separation of the clip unit 1C with respect to the clip introduction device 200 can be definitely performed. The distal-end side end portion 32b of the second wing 32C of the pressing tube 3C is disposed at the outside in the radial direction R with respect to the second fixed end 32a at the proximal-end side A2 of the second wing 32C in the state in which there is no external force applied. Accordingly, during the connection step, the connection member is not caught by the second wing 32C so at to be smoothly inserted into the pressing tube 3C from the proximal-end side A2.

As described above, the third embodiment of the present disclosure has been described in detail with reference to the drawings; however, the specific configuration is not limited to the present embodiment, and design changes and the like are included within the scope of the present disclosure. Also, the configurational elements shown in the present embodiment may be combined with the embodiments and the modification examples shown above as appropriate.

What is claimed is:
1. A clip unit, comprising:
    a clip, the clip including:
        a plurality of arms movable between an open position and a closed position; and
    a tube, the tube including:
        a tube main body configured to contain at least a part of the clip,
        a first wing, and
        a second wing,
    wherein the first wing is connected to the tube main body and the second wing is connected to the first wing,
    wherein the first wing is elastically deformable relative to the tube main body in a radial direction of the tube main body, and the first wing is biased radially inward toward an inner region of the tube main body, and
    wherein the second wing is elastically deformable relative to the first wing in the radial direction of the tube main body, and the second wing is biased radially outward toward an outside of the tube main body.
2. The clip unit according to claim 1, wherein the tube further includes a third wing connected to the tube main body, and
    wherein the third wing is located distally in a longitudinal direction of the tube main body relative to the second wing.

3. The clip unit according to claim 1, further comprising a connector inserted into the tube main body and detachably connected to the clip,
wherein, when the first wing engages the connector, a distal end of the second wing is located radially outward from an outer circumferential surface of the tube main body, and
wherein, when the first wing is spaced apart from the connector, the entire second wing is located within the inner region of the tube main body.

4. The clip unit according to claim 1, wherein, in a longitudinal direction of the tube main body, a distal end side of the first wing is connected to the tube main body, and a proximal end side of the second wing is connected to the first wing.

5. The clip unit according to claim 4, wherein the proximal end side of the second wing is connected to a proximal end of the first wing.

6. The clip unit according to claim 5, wherein the tube includes a third wing,
wherein, in the longitudinal direction of the tube main body, a distal end side of the third wing is connected to the tube main body,
wherein the third wing is located distally in a longitudinal direction of the tube main body relative to the second wing, and
wherein the first wing and the third wing are provided at different positions in the longitudinal direction in an outer surface of the tube main body.

7. The clip unit according to claim 1, wherein, in a longitudinal direction of the tube main body, a proximal end side of the first wing is connected to the tube main body, and a proximal end side of the second wing is connected to the distal end side of the first wing.

8. The clip unit according to claim 7, wherein the tube further includes a third wing,
wherein, in the longitudinal direction of the tube main body, a distal end side of the third wing is connected to the tube main body,
wherein the third wing is located distally in a longitudinal direction of the tube main body relative to the second wing, and
wherein the first wing and the third wing are provided at different positions in the longitudinal direction in an outer surface of the tube main body.

9. A clip delivery device, comprising:
a sheath;
a clip, the clip including:
a plurality of arms movable between an open position and a closed position;
a tube, the tube including:
a tube main body configured to contain at least part of the clip,
a first wing, and
a second wing;
a connector inserted into the tube main body and detachably connected to the clip; and
a wire inserted into the sheath and detachably connected the connector,
wherein the first wing is connected to the tube main body and the second wing is connected to the first wing,
wherein the first wing is elastically deformable relative to the tube main body in a radial direction of the tube main body, and the first wing is biased radially inward toward an inner region of the tube main body, and
wherein the second wing is elastically deformable relative to the first wing in the radial direction of the tube main body, and the second wing is biased radially outward toward an outside of the tube main body.

10. The clip delivery device according to claim 9, wherein the tube further includes a third wing connected to the tube main body, and
wherein the third wing is located distally in a longitudinal direction of the tube main body relative to the second wing.

11. The clip delivery device according to claim 9, wherein, when the first wing engages the connector, a distal end of the second wing is located radially outward from an outer circumferential surface of the tube main body, and
wherein, when the first wing is spaced apart from the connector, the second wing is located within the inner region of the tube main body.

12. The clip delivery device according to claim 9, wherein, when the first wing engages the connector and when the first wing and the connector engage a distal end portion of the sheath, the second wing is located radially outward from an outer circumferential surface of the tube main body.

13. The clip delivery device according to claim 12, wherein the second wing engages a distal end tip of the sheath.

14. The clip delivery device according to claim 9, wherein, in a longitudinal direction of the tube main body, a distal end side of the first wing is connected to the tube main body, and a proximal end side of the second wing is connected to the first wing.

15. The clip delivery device according to claim 14, wherein the proximal end side of the second wing is connected to a proximal end of the first wing.

16. The clip delivery device according to claim 15, wherein the tube includes a third wing,
wherein, in the longitudinal direction of the tube main body, a distal end side of the third wing is connected to the tube main body,
wherein the third wing is located distally in a longitudinal direction of the tube main body relative to the second wing, and
wherein the first wing and the third wing are provided at different positions in the longitudinal direction of the tube in an outer surface of the tube main body.

17. The clip delivery device according to claim 9, wherein, in a longitudinal direction of the tube main body, a proximal end side of the first wing is connected to the tube main body, and a proximal end side of the second wing is connected to a distal end side of the first wing.

18. The clip delivery device according to claim 17, wherein the tube further includes a third wing,
wherein, in the longitudinal direction of the tube main body, a distal end side of the third wing is connected to the tube main body,
wherein the third wing is located distally in a longitudinal direction of the tube main body relative to the second wing, and
wherein the first wing and the third wing are provided at different positions in an outer surface of the tube main body.

19. A method of loading a clip unit into an applicator, comprising:
connecting the clip unit and a wire, wherein the clip unit includes a clip, a tube configured to contain at least part of clip, and wherein the tube includes a first elastic portion;
pulling the wire proximal to a sheath, wherein the wire is inserted through the sheath through; and housing the tube in the sheath,
wherein, when housing the tube in the sheath, a distal end of the first elastic portion presses in a radially inward direction of the tube.

20. The method of loading the clip unit into an applicator according to claim 19, wherein the tube further includes a second elastic portion,
wherein the second elastic portion is located distally in a longitudinal direction of the tube relative to the first elastic portion, and
wherein, when housing the tube in the sheath, the second elastic portion presses in a radially outward direction of the tube.

* * * * *